US006180767B1

(12) United States Patent
Wickstrom et al.

(10) Patent No.: US 6,180,767 B1
(45) Date of Patent: Jan. 30, 2001

(54) PEPTIDE NUCLEIC ACID CONJUGATES

(75) Inventors: Eric Wickstrom, Philadelphia, PA (US); Soumitra Basu, New Haven, CT (US)

(73) Assignee: Thomas Jefferson University, Philadelphia, PA (US)

( * ) Notice: Under 35 U.S.C. 154(b), the term of this patent shall be extended for 0 days.

(21) Appl. No.: 08/779,072

(22) Filed: Jan. 7, 1997

Related U.S. Application Data
(60) Provisional application No. 60/009,747, filed on Jan. 11, 1996.

(51) Int. Cl.[7] .......................... C07H 19/00; C07H 21/02; C07H 21/00; C07H 21/04

(52) U.S. Cl. .......................... 536/22.1; 435/6; 536/23.1; 536/25.3; 536/25.31; 536/25.32; 536/25.33; 536/25.34

(58) Field of Search .................... 536/22.1, 23.1, 536/25.3, 25.31, 25.32, 25.33, 25.34; 435/6

(56) References Cited

U.S. PATENT DOCUMENTS

| 5,108,921 | 4/1992 | Low et al. ................ 435/240.1 |
| 5,256,398 | * 10/1993 | McAfee et al. ................ 424/9 |
| 5,271,941 | 12/1993 | Cho-Chung ................ 424/450 |
| 5,705,333 | * 1/1998 | Shah et al. ................ 435/6 |
| 5,834,607 | * 11/1998 | Manoharan et al. ................ 536/22.1 |

FOREIGN PATENT DOCUMENTS

| WO 88/05077 | 7/1988 | (WO) . |
| WO 90/10448 | 9/1990 | (WO) . |
| WO 91/04753 | 4/1991 | (WO) . |
| WO 92/20702 | 11/1992 | (WO) . |
| WO 92/20703 | 11/1992 | (WO) . |
| WO 94/25477 | 11/1994 | (WO) . |

OTHER PUBLICATIONS

Pietrzkowski et al. "Roles of insulinlike growth factor 1(IGF–1) and the IGF–1 receptor in Epidermal growth factor–stimulated growth of 3T3 cells" Molecular and Cellular Biology, pp. 3883–3889, vol. 12, No. 9, Sep. 1992.*
Pietrzkowski et al. "Inhibition of cellular proliferation by peptide analogues of insulin–like growth factor 1" Cancer Research, vol. 52, pp. 6447–6451, Dec. 1992.*
Van Winkle et al. "Inhibition of transport system b$^{9+}$in blastocysts by inorganic and organic cations yields insight into the structue of its amino acid receptor site" Biochemica et Biophysica Acta, vol. 1025, pp. 215–224, 1990.*
Piccoli et al. "L–[$^3$H]Lysine binding to rat retinal membrane: I. Quantitative determination and characterization of the binding sites" Neurochemical research, vol. 11, No. 12, pp. 1707–1717, 1986.*
Christensen et al., *Journal of Peptide Science*, 3: 175–183 (1995).
Pardridge et al., *Proc. Natl. Acad. Sci. USA*, 92: 5592–5596 (Jun. 1995).
Buchardt et al., *Tibtech*, 11: 384–386 (1993).

(List continued on next page.)

*Primary Examiner*—Jezia Riley
(74) *Attorney, Agent, or Firm*—Seidel, Gonda, Lavorgna & Monaco, PC

(57) ABSTRACT

Peptide nucleic acid (PNA) oligomers are conjugated to a ligand which is capable of binding to a cell surface receptor. The ligand facilitates cellular uptake of the PNA oligomer. Where the ligand is a peptide, the conjugate may be produced as a unitary molecule by first synthesizing the peptide ligand by solid phase or solution peptide synthesis, followed by synthesis of the PNA oligomer as an extension of the peptide ligand. The PNA oligomer base sequence is selected to hybridize to a target polynucleotide sequence by either triplex (dsDNA) or duplex (ssDNA; RNA) formation.

34 Claims, 6 Drawing Sheets

(3 of 6 Drawing Sheet(s) Filed in Color)

OTHER PUBLICATIONS

Noble et al., *Drug Development Research* 34:184–195 (1995).

Leamon et al., *Proc. Natl. Acad. Sci. USA* 88: 5572–5576 (1991).

Citro et al., *Proc. Natl. Acad. Sci. USA*, 89: 7031–7035 (1992).

Zon, "Pharmaceutical Considerations" in *Oligodeoxynucleotides Antisense Inhibitors of Gene Expressionion*, (J.S. Cohen, ed.) CRC Press, Inc., Boca Raton, FL, 1989, pp. 233–247.

Wagner et al., *Proc. Natl. Acad. Sci. USA*, 87: 3410–3414 (1990).

* cited by examiner

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) SEQUENCE DESCRIPTION: SEQ ID NO:1:

Gly Gly Gly Gly Cys Ser Lys Cys
1            5

(2) INFORMATION FOR SEQ ID NO:2:

(i) SEQUENCE CHARACTERISTICS:
        (A) LENGTH: 15 nucleotides
        (B) TYPE: nucleic acid
        (C) STRANDEDNESS: single
        (D) TOPOLOGY: linear (ii) SEQUENCE DESCRIPTION: SEQ ID NO:2:

TCCGGAGCCA GACTT                                                  15

(2) INFORMATION FOR SEQ ID NO:3:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) SEQUENCE DESCRIPTION: SEQ ID NO:3:

Cys Arg Arg Ser Ser Ser Gly Tyr Gly Thr Gly Cys
1            5                10

(2) INFORMATION FOR SEQ ID NO:4:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) SEQUENCE DESCRIPTION: SEQ ID NO:4:

Gly Cys Ser Lys Ala Pro Lys Leu Pro Ala Ala Leu Cys
1            5                10

(2) INFORMATION FOR SEQ ID NO:5:

(i) SEQUENCE CHARACTERISTICS:
        (A) LENGTH: 12 nucleotides
        (B) TYPE: nucleic acid
        (C) STRANDEDNESS: single
        (D) TOPOLOGY: linear (ii) SEQUENCE DESCRIPTION: SEQ ID NO:5:

CCGCTTCCTT TC                                                      12

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) SEQUENCE DESCRIPTION: SEQ ID NO:6:

Gly Gly Gly Gly Cys Ala Ala Cys
1            5

(2) INFORMATION FOR SEQ ID NO:7:

(i) SEQUENCE CHARACTERISTICS:
        (A) LENGTH: 12 nucleotides
        (B) TYPE: nucleic acid
        (C) STRANDEDNESS: single
        (D) TOPOLOGY: linear (ii) SEQUENCE DESCRIPTION: SEQ ID NO:7:

```
GAAAGGAAGC GG                                                   12
```

(2) INFORMATION FOR SEQ ID NO:8:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) SEQUENCE DESCRIPTION: SEQ ID NO:8:

```
Cys Ser Lys Ala Pro Lys Leu Pro Ala Ala Tyr Cys
1               5                   10
```

PEPTIDE NUCLEIC ACID CONJUGATES

CROSS-REFERENCE TO RELATED APPLICATION

Priority from U.S. provisional patent application Ser. No. 60/009,747, filed Jan. 11, 1996, is claimed.

REFERENCE TO GOVERNMENT GRANT

The invention described herein was supported in part by National Institutes of Health grant UOI-CA60139. The United States Government has certain rights in the invention.

FIELD OF THE INVENTION

The invention relates to the inhibition or regulation of gene expression with oligonucleotides. More particularly, the invention relates to conjugates of peptide nucleic acids and molecules which enhance cellular uptake, and the use of such conjugates to selectively target specific cell types.

BACKGROUND OF THE INVENTION

DNA therapeutics show great potential for gene-specific, nontoxic therapy of a wide variety of disease. The deoxyribose phosphate backbone of DNA has been modified in a number of ways to improve nuclease stability and cell membrane permeability (Knorre et al. (1994) *Design and Targeted reactions of Oligonucleotide Derivatives*, CRC Press, Boc a Raton, Fla.). Recently, a new class of compound, peptide nucleic acids (PNA) has shown potential as an antisense agent (Nielsen et al *Science,* 254, 1497–1500, 1991). PNAs comprise nucleic acid mimics in which the sugar-phosphate backbone is replaced with a backbone based on amino acids. PNAs generally exhibit sequence-specific binding to DNA and RNA with higher affinities and specificities than unmodified DNA. They are resistant to nuclease and protease attack. Melting temperatures of their duplexes with DNA or RNA are much higher than any of the known DNA compounds, both modified and unmodified. Recently, the solution structure of PNAs has also been determined by nuclear magnetic resonance (Brown et al., *Science* 265, 777–780, 1994).

The PNAs may be synthesized inexpensively on a large scale. PNAs may be synthesized by either solution phase or solid phase methods adapted from peptide synthesis. For example, PNAs can be synthesized from four protected monomers containing thymidine, cytosine, adenine and guanine via solid-phase peptide synthesis, by a modification of the Merrifield method (Merrifield, *J. Am. Chem. Soc.* 85, 2149–2154, 1963; Merrifield, *Science* 232, 341–347, 1986) employing, for example, BOC-Z protected monomers (Christensen et al., *J. Peptide Science* 3, 175–183, 1995).

PNAs recognize DNA and RNA in a sequence specific manner and form complexes which can be characterized by biophysical methods. The binding motif is context dependent; homopyrimidine PNAs combine with complementary polypurine targets to form stoichiometric 2:1 complexes, whereas PNAs containing both purine and pyrimidine bases afford a 1:1 heteroduplex with mis-match sensitivity comparable to that found in double-stranded (ds)DNA. The 2:1 complexes are formed when a second strand of the PNA binds the major groove of a PNA-DNA duplex through Hoogsteen base pairing. Thus, the triplex is comprised of a PNA/DNA duplex (formed by Watson-Crick hydrogen bonds) with a second PNA strand lying in the major grove of the duplex (held by Hoogsteen hydrogen bonds). These triplex complexes are so stable that "strand invasion" of dsDNA is possible. Binding of the PNA results in formation of a D-loop in the dsDNA. This characteristic is believed useful to manipulate gene expression at the transcriptional level. These 2:1 and 1:1 complexes mediate the antigene and antisense effects of PNAs via the steric blockade of enzyme complexes responsible for DNA transcription, cDNA synthesis, and RNA translation (Noble et al., *Drug Development Research* 34:184–195, 1995). PNAs may be used as antisense or antigene drugs, exploiting the sequence-dependent binding of the PNA portion to single stranded nucleic acids, particularly mRNA, or double-stranded dsDNA, respectively.

Although the biophysical data are very much in favor of the PNAs becoming very successful as nucleic acid binding agents, they suffer from a vital limitation in that they are taken up by cells very poorly.

Abbreviations

The following abbreviations may be used herein: A, adenine; aeg, 2-aminoethylglycine; AFP, alpha-fetoprotein; Bzl, benzyl; BOC, 1,-1-dimethylethoxycarbonyl; BHOC, benzhydryloxycarbonyl; C, cytosine; DECA, diethylcyclohexylamine; DIEA, diisopropylethylamine; DMAP, 4-dimethylaminopyridine; DMF, N-N-dimethylformamide; EDCHA, ethyldicyclohexylamine; EGF, epidermal growth factor; G, guanine; FBS, fetal bovine serum; FITC, fluorescein isothiocyanate; FMOC, (9H-fluoren-9-ylmethoxy); HATU, O-(7-azabenzotriazolyl)-1,1,3,3-tetramethyluronium hexafluorophosphate; HBTU, O-(benzotriazol-1-yl)-1,1,3,3-tetramethyluronium hexafluorophosphate; HDPU, O-(1,2-dihydro-2-oxo-1-pyridyl)-N,N,N',N'-bis(tetramethylene)uronium hexafluorophosphate; HOBt, 1-hydroxybenzotriazole; HGR, heregulin; IGF1, insulin growth factor-1; IGF1R, insulin growth factor receptor; MDCHA, methyldicyclohexylamine; MOB, 4-methoxybenzyl; NGF, nerve growth factor; NMP, N-methylpyrrolidine; PBS, phosphate buffered saline; PNA, peptide nucleic acid; PyBOP, benzotriazolyl-tris-pyrrolidino-phosphonium hexafluorophosphate; Rapoport's reagent, benzyloxycarbonyl-N'-methylimidazole triflate; ST, *E. coli* heat-stable enterotoxin; T, thymine; TBTU, O-(benzotriazol-1-yl)-1,1,3,3 -tetramethyluronium tetrafluoroborate; TGF, transforming growth factor; TLC, thin layer chromatography; Z, phenylmethoxycarbonyl.

SUMMARY OF THE INVENTION

According to the present invention, a conjugate is provided comprising a peptide nucleic acid (PNA) oligomer conjugated to a ligand which is capable of binding to a cell surface receptor. The oligomers bind complementary DNA or RNA strands through the bases which are linked to a peptide backbone. The sequence of the bases specifies the target nucleic acid to which the oligomer binds.

According to one preferred embodiment of the invention, the PNA oligomer has a subunit sequence such that the oligomer is capable of forming (i) a triplex with a dsDNA segment or (ii) a duplex with a ssDNA segment or mRNA segment, to inhibit expression of a gene. According to another preferred embodiment, the peptide nucleic acid oligomer has a subunit sequence capable of (i) or (ii), to inhibit expression of a gene which encodes a cell receptor for the ligand. The invention further provides a method for inhibiting expression of a gene in an organism comprising administering such a conjugate to an organism.

The invention is also a method for killing a pathogenic organism, such as a virus, a bacteria or a eukaryotic parasite, comprising contacting said organism with a conjugate as described above, which conjugate binds to a target polynucleotide sequence of said pathogenic organism.

DESCRIPTION OF THE FIGURES

The file of this patent contains at least one drawing executed in color. Copies of this patent with color drawing(s) will be provided by the Patent and Trademark Office upon request and payment of necessary fee.

FIG. 1B is a fluorescence image; FIG. 1A is a phase contrast image of the same field.

FIG. 5 also contains the melting temperature curve for the duplex consisting of the peptide nucleic acid H-Gly-CCGCTTCCTTTC-CONH$_2$ (H-Gly-SEQ ID NO:5-CONH$_2$) with the same complementary sequence (broken lines).

DETAILED DESCRIPTION OF THE INVENTION

Figures 1A, 1B:
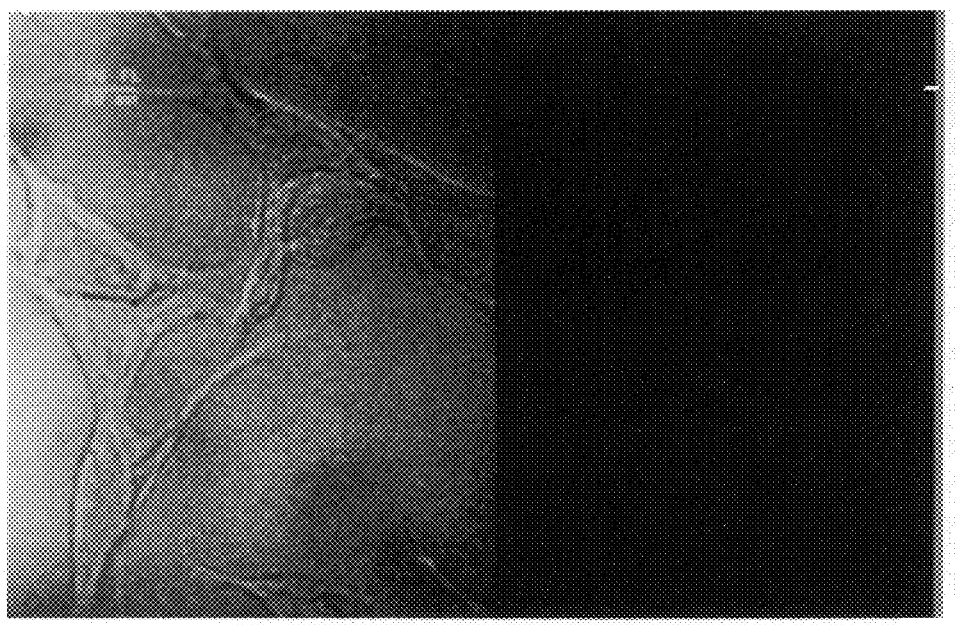
FIGS. 1A and 1B are confocal microscopic photographs of P6 cells incubated with fluorescein.
Figures 2A, 2B:
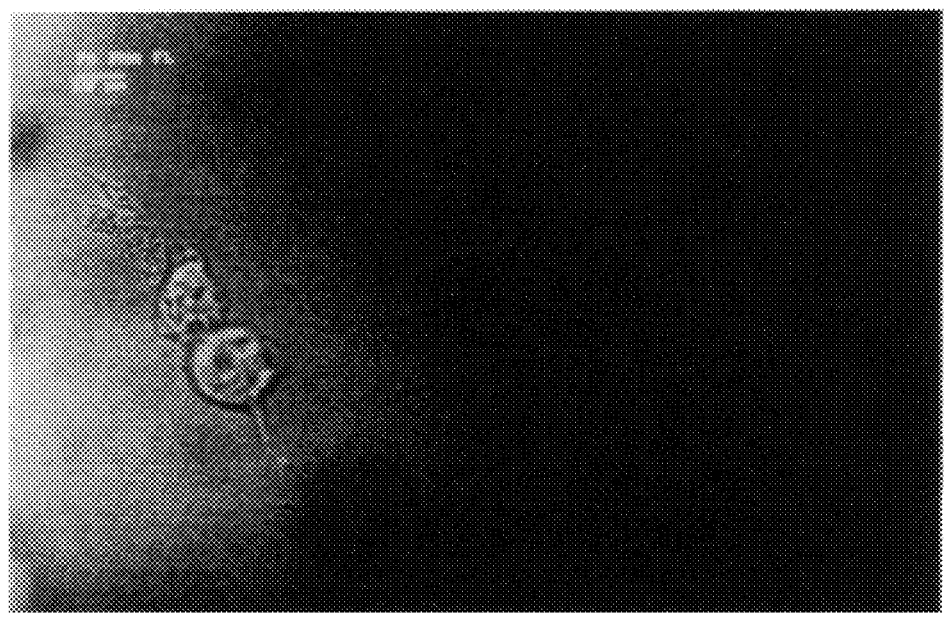
FIGS. 2A and 2B are similar to FIGS. 1A and 1B, except that the P6 cells were exposed to the fluoresceinyl-PNA having the sequence (H -Gly-CCGCTTCCTTTC-CONH$_2$ (H-Gly-SEQ ID NO:5-CONH$_2$), complementary to the nucleotide sequence spanning codons 706–709 of the IGF1R mRNA.

According to the present invention a PNA oligomer is conjugated to a ligand having a cognate receptor on the surface of a cell. The ligand facilitates the penetration and transport of the conjugate into the cell by receptor-mediated uptake.

The PNA oligomer portion of the conjugate is a strand, analogous to a nucleic acid strand, comprising a sequence of naturally occurring or non-naturally occurring organic bases covalently linked by a backbone. Whereas in conventional nucleic acids the backbone consists of a series of ribosyl or deoxyribosyl moieties, the sugar backbone is replaced in PNAs by a backbone substantially comprising polyamide, polythioamide, polysulfinamide or polysulfonamide. Thus, the peptide nucleic acid may be viewed as a strand of bases covalently bound by linking moieties comprising amide, thioamide, sulfinamide or sulfonamide linkages. Most preferably, the linking moieties in the backbone comprise N-ethylaminoglycine units. At least some of the bases are capable of hydrogen bonding with complementary bases of a target nucleic acids segment.

The PNA oligomer portion of the conjugates of the present invention comprise at least one peptide nucleic acid subunit of the formula:

$$\text{(I)}$$

wherein:

L is one of the adenine, thymine, cytosine or guanine heterocyclic bases of the oligomer;

C is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, $(C_2–C_6)$ alkyl, aryl, aralkyl, heteroaryl, hydroxy, $(C_1–C_6)$ alkoxy, $(C_1–C_6)$ alkylthio, $NR^3R^4$ and $SR^5$, where each of $R^3$ and $R^4$ is independently selected from the group consisting of hydrogen, $(C_1–C_4)$ alkyl, hydroxy- or alkoxy- or alkylthio-substituted $(C_1–C_4)$ alkyl, hydroxy, alkoxy, alkylthio and amino; and $R^5$ is hydrogen, $(C_1–C_6)$ alkyl, hydroxy-, alkoxy-, or alkylthio-substituted $(C_1–C_6)$ alkyl, or $R^6$ and $R^7$ taken together complete an alicyclic or heterocyclic system;

D is $(CR^6R^7)_z$ where $R^6$ and $R^7$ are as defined above;

each of y and z is zero or an integer from 1 to 10, the sum y+z being greater than 2 but not more than 10;

G is —NR$^3$CO—, —NR$^3$CS—, —NR$^3$SO— or —NR$^3$SO$_2$—, in either orientation, where $R^3$ is as defined above;

each pair of A and B is selected such that:
(a) A is a group of formula (IIa), (IIb) or (IIc) and B is N or $R^3N^+$; or
(b) A is a group of formula (IId) and B is CH;

$$\text{(IIa)}$$

-continued

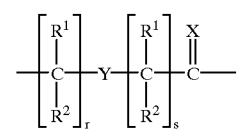

(IIb)

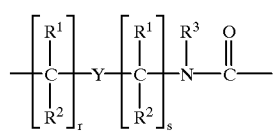

(IIc)

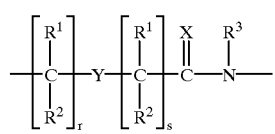

(IId)

where:

X is O, S, Se, $NR^3$, $CH_2$ or $C(CH_3)_2$;

Y is a single bond, O, S or $NR^4$;

each of p and q is zero or an integer from 1 to 5, the sum p+q being not more than 10;

each of r and s is zero or an integer from 1 to 5, the sum r+s being not more than 10;

each $R^1$ and $R^2$ is independently selected from the group consisting of hydrogen, ($C_1$–$C_4$) alkyl which may be hydroxy- or alkoxy- or alkylthio-substituted, hydroxy, alkoxy, alkylthio, amino and halogen.

"Subunits", as used herein, refers to basic units which are chemically similar and which can form polymers. Repeating basic units form polymers referred to as "oligomers". The PNA oligomer portion of the conjugates of the present invention may comprise an oligomer in which substantially all subunits of the oligomer are subunits as described in Formula I. The PNA oligomer may also comprise one or more subunits which are naturally occurring nucleotides or nucleotide analogs as long as at least one subunit satisfies Formula I. Thus, "PNA oligomers" as used herein may refer to a range of oligomers, from oligomers comprising only one PNA subunit as defined in Formula I to oligomers in which every subunit is a PNA subunit as defined in Formula I. The amino acids which form the backbone may be identical or different.

Those subunits which are not PNA subunits comprise naturally occurring bases, sugars, and intersugar (backbone) linkages as well as non-naturally occurring portions which function similarly to naturally occurring portions.

Sequences of oligomers are defined by reference to the L group (for PNA subunits) or nucleobase (for nucleotide subunits) at a given position. Thus, for a given oligomer, the nomenclature is modeled after traditional nucleotide nomenclature, identifying each PNA subunit by the identity of its L group such as the heterocycles adenine (A), thymine (T), guanine (G) and cytosine (C) and identifying nucleotides or nucleosides by these same heterocycle residing on the sugar backbone. The sequences are conveniently provided in traditional 5' to 3' or amino to carboxy orientation.

The PNA oligomer portion of the inventive conjugate may range in size from about 8 to about 60 subunits in length. In other embodiments of the present invention, oligomers may range in size from about 10 to about 30 subunits in length. In still other embodiments of the present invention oligomers may range in size from about 12 to about 25 subunits in length. In yet further embodiments of the present invention, oligomers may range in size from about 12 to about 20 subunits in length.

Methods for the preparation of peptide nucleic acids are described in the following, the entire disclosures of which are incorporated herein by reference: International Patent Applications PCT/EP92/01219 (WO 92/20702), PCT/EP92/01220 (WO 92/20703), PCT/IB94/00142 (WO 94/25477), PCT/US94/06620 (WO 94/28720), PCT/US94/07319 (WO 95/01370), and PCT/US94/08465 (WO 95/03833).

Essentially, PNAs are synthesized by adaptation of solution or solid phase peptide synthesis procedures. The synthons are monomer amino acids or their activated derivatives, protected by standard protecting groups. The state of the art in PNA synthesis is extensively reviewed in PCT/US94/08465, page 11, line 6—page 23, line 7, which is specifically incorporated herein by reference.

A PNA oligomer having the preferred backbone, that is, a backbone formned by N-ethylaminoglycine units, is formed by linking the following commercially available (PerSeptive Biosystems, Framingham, Mass.) BOC and Z-protected T, A, C, and G monomers: IIIa, BOC-T-OH; IIIb, BOC-A(Z)-OH; IIId, BOC-C(7)-OH; and IIIc, BOC-G(Z)-OH:

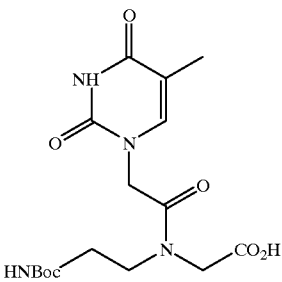

IIIa

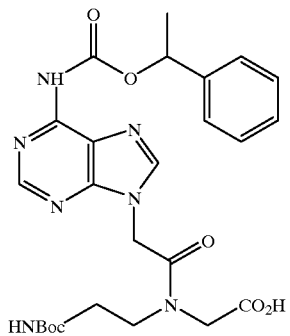

IIIb

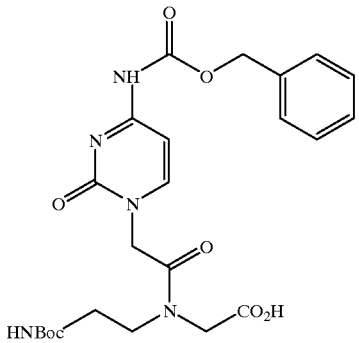

IIIc

IIId

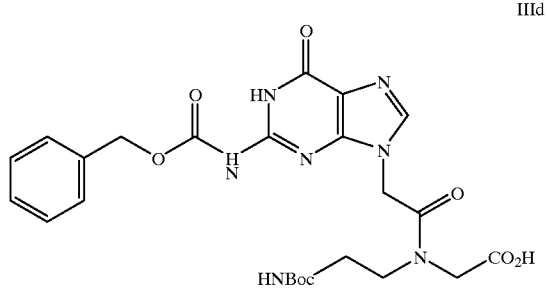

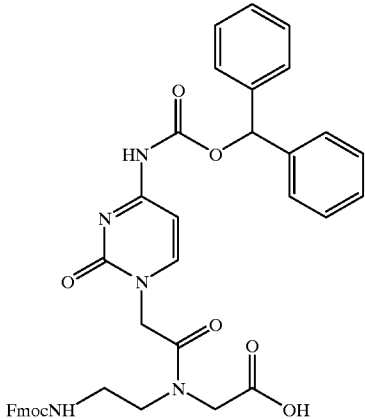

IVc

IVd

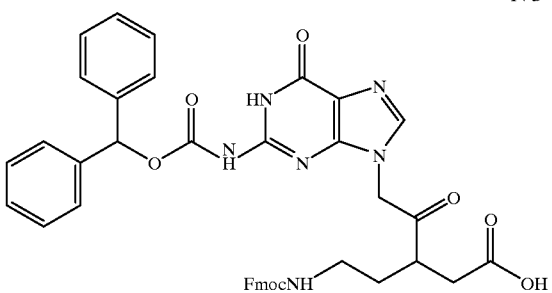

Methods for the solid-phase synthesis of peptide nucleic acids containing these monomers are described in Christensen et al., *J. Peptide Science* 3, 175–183, 1995, the entire disclosure of which is incorporated herein by reference.

As an alternative to BOC chemistry, the PNA may be synthesized via FMOC chemistry by linking the following commercially available (PerSeptive Biosystems) FMOC and BflOC-protected T, A, C and G PNA monomers: IVa, FMOC-T-OH; IVb, FMOC-A(BHOC)-OH; IVc, FMOCC(BHOC)-OH; and IVd, FMOC-G(BHOC)-OH:

IVa

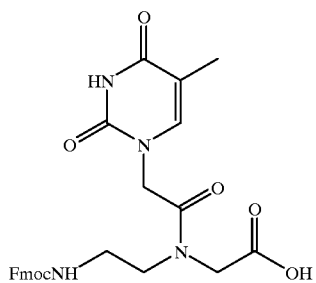

IVb

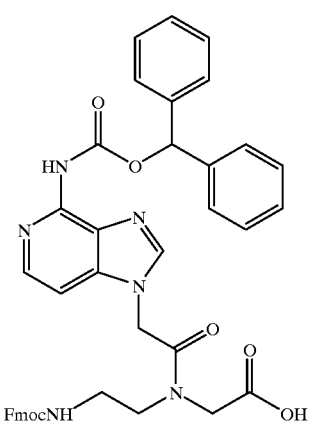

The ligand, which comprises any chemical substance which is capable of binding to a cell surface receptor, may be attached to the PNA oligomer by conventional chemical coupling techniques, at any location on the PNA oligomer. The desirability of the attachment site will depend on the mode of interaction of the ligand with its receptor and the chemical nature of the ligand. Preferably, the ligand is attached to either terminal subunit of the PNA oligomer, although conjugation to an internal subunit is not excluded. The linking moiety may comprise any conventional chemical moiety. The selection of the linker will depend primarily on the chemical nature of the ligand. The linking group for coupling the PNA oligomer and ligand may comprise, for example an appropriate amine or amido group.

While the ligand molecule may be attached directly to the PNA oligomer, it is preferred for steric reasons that the two molecules are coupled in a spaced relation, through inclusion of a linker moiety. Preferably, the ligand is separated from the DNA oligomer by a distance of from about 10 to about 30 Å. Linker moieties are selected accordingly. The linker may comprise any chemical group which is compatible with the ligand and PNA oligomer and which does not adversely affect either conjugate uptake or oligomer hybridization to the target nucleic acid segment.

According to a preferred embodiment of the invention wherein the ligand is a peptide and the PNA oligomer is synthesized directly on the peptide by chain extension, the linker may comprise one or more amino acids, most preferably, a stretch of homo-glycine, es, (Gly)$_4$. Alternatively, an appropriate linker may be included in the growing chain between the peptide and PNA oligomer by incorporating a modified amino acid at the PNA/peptide junction which includes a linker moiety, em, an appropriate methylene bridge-containing moiety. One such amino acid is N-$\epsilon$-FMOC-aminocaproic acid.

Where FMOC chemistry is used to synthesize the PNA oligomer, and the ligand is a peptide, the PNA oligomer may be readily attached to the peptide's amino or carboxy terminus. If it is desired to attach the PNA oligomer to an internal amino acid residue of the peptide ligand, an $\epsilon$-(N-tBOC)-lysine residue would be included in the peptide. After completion of peptide synthesis by FMOC coupling, and cleaving of the terminal FMOC group, the $\epsilon$-(N-tBOC)-lysine is deprotected with acid, and can serve as the attachment site for BOC coupling of a PNA oligomer.

According to one embodiment of the invention wherein the ligand comprises a peptide, the peptide is first synthesized by any of the known peptide synthesis methods. While the PNA oligomer and peptide ligand may be synthesized separately and then covalently coupled by and of the known reagents suitable for coupling proteinaceous compounds, it is preferred that the peptide ligand is synthesized first, followed by synthesis of the PNA oligomer as an extension of the peptide ligand. The amino acids used to form the peptide ligand may comprise D- or L-amino acids, or a mixture of both. Different coupling chemistries may be used for the peptide and PNA oligomer syntheses. However, for example, where BOC coupling is used for PNA oligomer synthesis and FMOC coupling is used for peptide synthesis, the protecting groups for the peptide are chosen in such a way as to be compatible with BOC coupling and BOC deprotection. Thus, for FMOC peptide synthesis followed by BOC PNA oligomer synthesis, FMOC amino-protected amino acids utilized in the peptide synthesis would include appropriate blocking groups on the amino acid side chains. Such fully protected amino acids include, for example, FMOC-Cys(MOB)-OH, wherein the native sulfhydryl group is protected by a methoxybenzyl group: FMOC-Lys (Z)-OH, wherein the native $\epsilon$-amino group is protected by a phenylmethoxycarbonyl group; and FMOC-Ser(Bzl)-OH, wherein the native hydroxyl group is protected by a benyl group. Other suitable side chain-protected FMOC amino acids are known to those skilled in the art. Following the completion of the PNA oligomer synthesis onto the peptide, the completed peptide/PNA oligomer conjugate is then finally deprotected and cleaved from its solid support.

Preferably, the entire peptide/PNA oligomer conjugate is synthesized by the same peptide synthesis chemistry. For example, it is possible to synthesize an entire PNA-oligomer/peptide conjugate via FMOC chemistry originally designed for peptide synthesis. FMOC-PNA subunits are commercially available (PerSeptive Biosystems, Framingham, Mass.).

Preferably, where the ligand is a peptide, at least one of the amino acids of the peptide is a D-amino acid. This has the effect of enhancing the conjugate's biological stability.

The ligand may comprise any chemical substance which is capable of binding or being bound by a cell surface receptor. While the receptor can be a receptor found on more than one cell type, according to one preferred embodiment of the invention, the receptor is specific to the cell type targeted. The receptor, and thus the ligand portion of the inventive PNA oligomer/ligand conjugate, is selected such that the receptor provides a pathway into the cell for the PNA oligomer attached thereto. In this manner, the poor cell uptake of the PNA oligomer is circumvented. Preferably, the conjugation of the PNA oligomer to the ligand does not substantially interfere with the ability of the ligand to bind its cognate cell receptor or gain entry into the cell.

The ligand may comprise, for example, a protein, a glycoprotein, a peptide, a steroid, a carbohydrate, a lipid or vitamin capable of binding or being bound by a cell surface receptor and being taken up into the cell. Examples of useful proteinaceous ligands include peptide hormones, antigens, antibodies, growth factors, cytokines, and peptide toxins. Most preferably, the ligand comprises a small peptide analog of a larger native receptor-binding peptide or polypeptide which retains the receptor-binding property of the native molecule. While the exact mechanism of uptake is not limiting on the scope of the present invention, it is contemplated that the mechanism of uptake of the inventive PNA oligomer/ligand conjugates will be one a mechanism of receptor-mediated endocytosis. Hence, the ligand is most advantageously selected such that it is capable of triggering endocytosis.

Examples of specific ligands include, for example, the vitamin folate, to take advantage of the natural endocytosis pathway for that molecule (Leamon and Low, *Proc. Natl. Acad. Sci. USA* 88, 5572–5576, 1991); the irontransport protein transferrin, to take advantage of the receptor-mediated uptake of transferrin-iron complexes by actively metabolizing cells (Wagner et al., *Proc. Natl. Acad. Sci. USA* 87, 3410–3414, 1990); any of the following substances described in PCT/EP87/00827 (WO 88/05077) as being useful targeting factors in the receptor mediated endocytosis of nucleic acids: epidermal growth factor (EGF); platelet-derived growth factors; urogastrone and analogues thereof; thyrotrypsin releasing hormone (TRH); nerve-growth factor (NGF); and any of the various specific viral factors, e.g., a specific viral antigen of the HIV virus (Maddon et al., *Cell* 47, 333, 1986) specific to the T4-receptor typical of T4 lymphocytes but which can be also be found on other cells; IgG; $\alpha_2$-macroglobulin; somatomedin C; thiodothyronine; and thrombine. The ligand may also comprise an antibody (inclusive of any fragment thereof retaining substantial antigen-binding ability) against a cell surface antigen. This is particularly relevant to the treatment of diseases, particularly various cancers, which are characterized by the cell surface expression of tumor-specific antigens.

Ligands which are believed particularly useful include for targeting in the practice of the present invention include the following and corresponding analogs which retain the receptor-binding property of the native ligand: IGF1; *Escherichia coli* heat-stable enterotoxins; arachidonic acid; EGF; transforming growth factor-$\alpha$ (TGF)-$\alpha$; and the various hereguiins (HRGs). By "analog" is meant any peptide which has a sequence homology of at least about 30% with respect to a corresponding segment of the native polypeptide from which the analog was derived. "Homology" has its accepted meaning to those skilled in the art of protein science. Generally, the analog is selected such that it will have the minimum size which retains ability to bind the corresponding cognate receptor. The peptide may comprise, for example, 5 to 50 amino acids, more preferably 5 to 30 amino acids, most preferably 5 to 15 amino acids. Peptide analogs of a particular native polypeptide are designated with respect to the corresponding native polypeptide. Thus, for example, by "IGF1 peptide" is meant a peptide analog of IGF1.

IGF1 binds its cognate cell-surface receptor IGF1R. The IGF1/IGF1R system plays a major role in development and cell cycle progression, and may play a role in the early phase of tumorigenesis. International patent application PCT/ US94/14576 (WO 95/16703) lists several publications indicating the role of IGF1 in cell proliferation. For instance, IGF1Rs are present in phytohemagglutinin activated T lymphocytes, Kozak et al., *Cell Immunol.*, 1009:318–331 (1987) and in K562 cells that are a human erythroleukemia cell line, Hizuka et al., *Endocrinol. Japon.*, 34:81–88 (1987). In fact, K562 cells grow vigorously in serum free media (SFM) containing only IGF1 or supraphysiological concentrations of insulin. An abundance of IGF1Rs has also been reported in lymphoblasts of human T cell leukemias, Lee et al., *J. Clin. Endocrinol. & Metabol.*, 62:28–35 (1986), and in HL60 cells, Pepe et al., *J. Cell Physiol.*, 133:219–227 (1987). The mRNA for IGF1R is overexpressed in HL60 cells. HL60 cells, as well as other cell lines, grow well in serum-free medium containing only insulin in supraphysiological concentrations. In Burkitt cells, the number of IGF1Rs increase between $G_1$ and S-3 phase, Hartman et al., *Leukemia*, 2:241–4 (1988). Stem cells and progenitor cells also seem to require IGF1 for growth. Goldring and Goldring, *Eucar. Gene Express.*, 1:301–326 (1991), list several references indicating that IGF1 increases the proliferation of keratinocytes, smooth muscle cells, osteoblasts, chrondrocytes and neuronal cells (see their Table 4). The IGF1R is induced by estrogens in breast cancer cell lines, Stewart et al., *J. Biol. Chem.*, 265:21172–8 (1990), Pekonen et al., *Cancer Res.*, 48:1343–7 (1988), Peyrat et al., *Cancer Res.*, 48:6429–33 (1988), Foekens et al., *Cancer Res.*, 49:5823–8 (1989), and the expression of IGF1R seems to correlate with the growth of breast cancer, at least just as well as the strogen receptors or the EGF receptor. Other tumors in which an increased expression of IGF1R or, at least, IGF1 binding sites, have been reported include small cell lung cancer, Kiefer et al., *Exp. Cell Res.*, 184:396–406 (1989), Minuto et al., *Cancer Res.*, 48:3716–9 (1988), Nakanishi et al., *J. Clin. Invest.*, 82:354–9 (1988), choriocarcinoma cells, Ritvos et al., *Endocrinology*, 122:395–401 (1988), malignant glioma, Gammeltoft et al., *Cancer Res.*, 48:1233–7 (1988), renal carcinoma, Pekonen et al., *Int. J. Cancer*, 43:1029–33 (1989), and neoplastic human endometrium, Talavera et al., *J. CancerRes.*, 50:3019–24 (1990). A role of IGF1R in growth has also been reported in human melanoma cells, Stracke et al., *J. Biol. Chem.*, 264:21544–9 (1989), and in tumors of neural origins such as neuroblastomas or pheochromocytomas, Ota et al., *Molec. Brain Res.*, 6:69–76 (1989) and Ota et al., *Cur. J. Biochem.*, 174:521–30 (1988).

When IGF1 binds to IGF1R, IGF1R undergoes autophosphorylation. The autophosphorylation is believed to be an important event in cell growth and proliferation. Thus, IGF1-induced autophosphorylation of IGF1R is believed to be involved in the undesirable cell growth and proliferation involved in the pathogenesis associated with diseases and disorders such as, for example, cancer, restenosis and asthma.

Antisense DNA down-regulation of IGF1R expression has been shown to inhibit the proliferation of tumor cell lines dependent on IGFR1 (Pietrzkowski et al., *Cell Growth Diff.* 3, 199–205, 1992). Similarly, it has been shown that the disulfide-bonded D-peptide Gly-Cys-Ser-Lys-Ala-Pro-Lys-Leu-Pro-Ala-Ala-Leu-Cys (SEQ ID NO:4), an analog of native IGF1 designed by molecular modeling to compete with the native ligand for binding to IGF1R, also inhibits the proliferation of tumor cell lines dependent on IGFR1 (Pietrzkowski et al., *Cancer Res.* 52, 6447–6451, 1992). The disulfide-bonded D-peptide Cys-Ser-Lys-Ala-Pro-Lys-Leu-Pro-Ala-Ala-Tyr-Cys (SEQ ID NO:8) inhibits the growth of certain cancer cell lines and competes with the natural ligand for binding to IGF1-R (Id.). The IGF1R cDNA sequence is set forth by Ullrich et al., *EMBO J.* 5:2503–2512 (1986), the entire disclosure of which is incorporated herein by reference. Various IGF1 peptides are disclosed in PCT/US93/04329 (WO 93/23067) and PCT/US94/14576 (WO 95/16703), the entire disclosures of which are incorporated herein by reference. These IGF1 peptides, up to 25 amino acids in length, comprise a sequence corresponding to at least a portion of the IGF1 C or D domain.

*Escherichia coli* heat-stable enterotoxins (ST) are small peptides of 18 or 19 amino acids that bind to specific cell surface receptors located on the intestinal brush border and activate guanylate cyclase, resulting in an increase in the intracellular cyclic guanosine 3',5'-monophosphate content of the cell. The receptors for ST are also expressed by primary and metastatic human colonic tumors in vivo, with structural and functional characteristics that are similar to those in normal human colon (Carrithers et al., *Gastroenterology* 107:1653–1661, 1994). Native ST may be purified from *E. coli* by known methods (Dreyfus et al., *Infect. Immun.*, 46:537–543, 1984; Thompson et al., *Anal. Biochem.*, 148:26–36, 1985). Smaller analogs of native ST may be designed and then tested for ST-receptor binding activity according to the method of Carrithers et al., supra, and references cited therein (Hugues et al., *Biochemistry* 30:10738–10745, 1991; Hugues et al., *Mol. Pharmacol.* 41:1073–1080, 1992; Crane et al., *Int. J. Biochem.* 25:557–566, 1993; Hakki et al., *Biochim. Biophys. Acta* 1151:223–230, 1993), and conjugated to PNA oligomers for uptake by cells expressing the ST receptor.

Alpha-fetoprotein (AFP) is a major serum glycoprotein and member of the group of carcinoembryonic antigens. AFP is formed during vertebrate embryonic development, and reappears in the serum of adults as a consequence of certain neoplastic pathological conditions (Abelev et al., *Adv. Cancer Res.*, 14:295–358, 1971; Ruoslathi & Seppälä, *Adv. Cancer Res.* 29:276–336, 1979). Mouse and human lymphoblastoid cell lines derived from T and B lymphomas express specific cell receptors for AFP, as well as normal human T cells (Torres et al., *J. Cell. Physiol.* 150:456–462, 1992). AFP is a transporter of fatty acids to actively dividing cells through a receptor-mediated mechanism. AFP reversibly binds fatty acids with high affinity. A fatty acid, such as arachidonic acid, or analogue thereof retaining the ability to be transported into cells via the AFP/receptor system, may be used as a ligand for transporting PNA oligomers into cells expressing the AFP receptor.

$p185^{erbB}$-2 (also known as HER-2 and neu), and $p180^{erbB-4}$ (also known as HER-4), are receptor-type kinases that are similar to $p170^{erbB-1}$ (also known as EGF receptor or HER-1). The ligands for $p170^{erbB-1}$ are EGF and transforming growth factor (TGF)-α.

The c-erbB2/neu proto-oncogene is frequently amplified in tumors and cell lines derived from tumors. The gene product is a potent oncoprotein when overexpressed in NIH 3T3 cells or transgenic mice, resulting in a predominance of mammary tumors (Muller et al., *Cell* 54:105–115, 1988; Bouchard et al., *Cell* 57:931–936, 1989). In addition, c-erbB2/neu gene amplification in human breast tumors is often associated with poor patient prognosis (Slamon et al., *Science* 235, 177–182, 1987 and 224, 707–712, 1989). The products of the c-erbB2/neu proto-oncogene and transforming genes differ by a single point mutation which changes a valine to a glutamic acid in the p185 protein's transmembrane region (Bargman et al., *Cell* 45, 649–657, 1986). This mutation is associated with enhancement of intrinsic protein-tyrosine kinase activity and increased oncogenic potential of the p185 protein (Bargman et al., *Proc. Natl. Acad. Sci. USA* 85, 5394–5398, 1988). Antisense DNA phosphorothioates against c-erbB2 mRNA have been observed to depress p185 levels and inhibit human breast cancer cell proliferation (Bertram et al., *Biochem. Biophys. Res. Commun.* 200, 661–667, 1994; Vaughn et al., *Proc. Natl. Acad. Sci. USA* 92, 8338–8342, 1995).

It has been shown that p180$^{erbB-4}$ binds heregulin (HRG)-α, a 45 kDa glycoprotein, and its related molecules HRG-β1, β2, and β3 (Nagata et al., *Embo J.* 13, 3517–3523, 1994). The HRGs have been isolated from the conditioned medium of MDA-MB-231 human breast carcinoma cells (Holmes et al., *Science* 256, 1205–1210, 1992). While no ligand has been yet identified for p185$^{erbB-2}$, it has been shown that HRG binding to the homologous receptor p180$^{erbB-4}$ activates p815$^{erbB-2}$ indirectly through transphosphorylation or receptor heterodimerization (Peles et al., *EMBO J.* 12:961–971, 1993; Plowman et al., *Nature* 366:473–475, 1993).

Peptide analogs of EGF, TGF-A and the HRGs, particularly small peptide analogs which retain the ability to bind the corresponding cognate receptor p170$^{erbB-1}$ or p$_{180}$$^{erbR-4}$, are advantageously used as ligands for delivery of PNA oligomers to cells expressing those receptors.

According to a preferred embodiment of the invention, the cell receptor which is utilized for receptor-mediated uptake is also targeted for downregulation. The subunit sequence of the PNA oligomer is selected such that the oligomer binds to either genomic DNA or mRNA encoding the receptor, to inhibit the expression of the receptor and thereby achieve a form of "self-quenching" receptor binding. This embodiment of the invention is particularly useful where the receptor expression has a role in the etiology of a specific disease state. Thus, for example, the ligand may comprise a synthetic peptide analog of IGF1R for the treatment of virtually any malignancy. Constitutive expression of IGF1 and IGF1R in BALB/c3T3 cells has been shown to abrogate all requirements for exogenous growth factors (Pietrzkowski et al., *Cell Growth Diff.* 3, 199–205, 1992).

According to another embodiment, the ligand may comprise a peptide analog of HRGA and the PNA oligomer is complementary to the mRNA encoding p185$^{erbB-2}$. Downregulation of c-erbB2/neu expression by administration of a conjugate comprising a peptide analog of HRGα conjugated to an "antisense" PNA oligomer complimentary to the c-erbB2/neu mRNA transcript would comprise an efficient tumor cell-specific anticancer agent for treatment of mammalian and ovarian malignancies.

The nucleic acid sequences targeted for PNA oligomer binding according to the practice of the present invention may comprise, for example, oncogene or proto-oncogene genomic DNA (through triplex formation) or mRNA (through duplex formation). For example, c-myc expression may be targeted for inhibition, for treatment of hematological, mammary and colorectal malignancies (Gazin et al., *EMBO J.*, 3:383–387, 1984). Ki-ras may be targeted for treatment of pancreatic, colorectal and pulmonary malignancies (Shimizu et al., *Nature* 304:497–500, 1983). Inhibition of c-myb expression is useful in the treatment of leukemias (U.S. Pat. No. 5,098,890), colorectal carcinoma (PCT/US92/04318) and melanoma (PCT/US92/09656). Expression of the hybrid oncogene bcr-abl may be targeted for treatment of Philadelphia chromosome-positive leukemias (PCT/US92/05035). Other oncogene and proto-oncogene targets for expression inhibition are known to those skilled in the art.

Yet another attractive therapeutic target is the human telomerase RNA template, which has recently been cloned (Feng et al., *Science* 269:1236–1241, 1995). It has been demonstrated that human telomerase is a critical enzyme for the long-term proliferation of immortal tumor cells. HeLa cells transfected with an antisense human telomerase RNA component began to die after 23–26 doublings (id.). The telomerase RNA template is an attractive target for hybridization by a PNA oligomer, for treatment of virtually any malignancy.

The conjugates of the present invention may also be useful in the treatment of viral infections. Targets for treatment of viral infection include nucleic acids of human immunodeficiency virus (Ratner et al., *Nature* 313:277–284, 1985), herpes simplex virus (Smith et al., *Proc. Natl. Acad. Sci. USA* 83:2787–2791, 1986)), influenza virus (Leiter et al., *Proc. Natl. Acad. Sci. USA* 87:3430–3434, 1990)) and rabies virus.

The conjugates of the present invention may also find utility in the treatment of autoimmune disorders. Inadvertent production of antibodies against normal body tissues and structures results in degeneration of the target tissue (Davis, *Annul. Rev. Biochem.* 59:475–496, 1990). Conjugates comprising PNA oligomers complementary to unique sequences in the autoimmune B-cell immunoglobulin genes or T-cell receptor genes may be capable of suppressing production of autoimmune antibodies or receptors by the particular plasma cell clonal lines involved. This approach may be of value in treating arthritis, systemic lupus erythromatosus, and myasthenia gravis, among other autoimmune disorders. PNA oligomer therapy may also be of value in suppressing the graft rejection response without compromising an individual's entire immune system.

The conjugates of the present invention may also be useful in the treatment of endocrinological disorders. Circulatory renin has a well-established role in blood pressure and volume homeostasis. Tissue renin regulates the production of local angiotensis which exerts paracrine/autocrine influences on local tissues. Renin cleaves a$_2$-globulin to give the decapeptide proangiotensin, from which the carboxy terminal dipeptide is removed by the enzyme angiotensinase to give angiotensin. PNA oligomers complementary to sequences of the renin, angiotensinase or vasopressin precursor DNA or mRNA may be useful in controlling hypertension.

Renal failure is yet another endocrine disorder which may be the subject of PNA oligomer treatment. Glomerulonephritis is an inflammation of the kidney characterized by accumulation of extracellular matrix within the damaged glomeruli, impaired filtration, and proteinuria. Animal models have shown that the disease is associated with increased production and activity of transforming growth factor-β1 (TGF-β1), an inducer of extracellular matrix production. Administration of anti-TGF-β1 at the time of induction of the glomerular disease suppresses the increased production of extracellular matrix and dramatically attenuates histological manifestations of the disease, providing direct evidence for a causal role of TGF-β1 in the pathogenesis of the disease (Border et al., *Nature* 346:, 371–374, 1990). Complementary PNA oligomer-induced inhibition of TGF-β31 expression is an attractive therapy for glomerulonephritis.

Targeting of human growth hormone expression for inhibition by PNA oligomers is a potential treatment for acromegaly.

Neurological diseases such as Alzheimer's disease may be treatable using conjugates comprising PNA oligomers targeting mutant β-amyloid protein expression. It has been suggested that the monoamine oxidases may play a role in some forms of mental illness. The cDNAs for the A and B forms of monoamine oxidase have been isolated and cloned (Bach et al., *Proc. Natl. Acad. Sci. USA* 85: 4934–4938, 1988). Expression of theses genes may be useful targets for inhibition by complementary PNA oligomers.

The conjugates of the invention may also be useful in the treatment of bacterial and parasitic infections. PNA oligomers complementary to the 3' terminus of bacterial 16S rRNA may prove useful in the treatment of antibiotic-resistant bacterial infections. Selective inhibition of *E. coli* protein synthesis and growth has been achieved by nonionic oligonucleotides complementary to the 3' end of 16S rRNA (Jayaraman et al., *Proc. Natl. Acad. Sci. USA* 78:1537–1541, 1981). The 16S rRNA 3' terminus of *Mycobacterium phlei* is a particularly attractive therapeutic target in antibiotic-resistant tuberculosis. PNA oligomers complementary to *Plasmodium falciparum* haem polymerase (Slater & Cerami, *Nature* 355:167–169, 1992) and the Trypanosoma 35-nucleotide leader (Cornelissen et al., *Nucleic Acids Res.*, 14:5605–5614, 1986) could be useful in the treatment of chloroquine-resistant malaria and sleeping sickness, respectively.

The conjugates of the invention may be potentially useful in the treatment of sickle cell anemia. Expression of fetal hemoglobiny (Sunshine et al., *Nature* 275:238–240, 1978) may be targeted for inhibition by creation of an open transcription bubble with a PNA oligomer (Møllegaard et al., *Proc. Natl. Acad. Sci. USA* 91:3892–3895, 1994).

PNA oligomers can target RNA or ssDNA to produce antisense-type regulation of gene expression or can target dsDNA. Sequence-specific PNA oligomer binding to dsDNA may proceed by triple helix formation which is limited to recognition of homoporine-homopyrimidine sequences, or by strand displacement. Strand displacement is superior to triplex formation in that it allows for recognition of any sequence by use of the four naturally occurring bases. Also, base recognition in strand displacement occurs at physiological conditions. Suitable binding sites for gene-targeting PNA oligomers include, for example, regulatory elements, most preferably the promoter. Alternatively, the target could be located downstream from the promoter, causing RNA polymerase to terminate transcription at this position thus forming a nonfunctional truncated mRNA and protein.

Complementary base hybridization can be utilized to target specific sequences in mRNA to block translation. Preferred mRNA targets include the 5' cap site, tRNA primer binding site, the translation initiation site, the mRNA donor splice site, and the mRNA acceptor splice site. See, e.g., Goodchild et al., U.S. Pat. No. 4,806,463.

Where the target polynucleotide comprises an mRNA transcript, PNA oligomers complementary to and hybridizable with any portion of the transcript are, in principle, effective for inhibiting translation. It is believed that translation is most effectively inhibited by blocking the mRNA at a site at or near the initiation codon. Thus, oligomers complementary to the 5'-region of the relevant mRNA transcript are preferred, such as, for example an oligomer capable of forming a duplex with a portion of the mRNA transcript lying within about 100 nucleotides, preferably about 50 nucleotides, upstream or downstream of the translation initiation codon. Oligomers complementary to the region, including the initiation codon (the first codon at the 5' end of the translated portion of the transcript), or codons adjacent the initiation codon, are preferred. One preferred target is the first about 100 nucleotides of the 5'-untranslated region.

While PNA oligomers complementary to the 5'-region of the target mRNA transcript are preferred, particularly the region including the initiation codon, it should be appreciated that useful oligomers are not limited to those complementary to the sequences found in the translated portion of the mRNA transcript, but also includes oligomers complementary to nucleotide sequences contained in, or extending into, the 5'- and 3'-untranslated regions.

In general, the PNA oligomer used in the practice of the present invention will have a subunit sequence which is completely complementary to a selected portion of the target polynucleotide. Absolute complementarity is not however required, particularly in larger oligomers. Thus, reference herein to a "subunit sequence complementary to" a target polynucleotide does not necessarily mean a sequence having 100% complementarity with the target segment. In general, any PNA oligomer having sufficient complementarity to form a stable duplex or triplex with the target that is, an oligomer which is "hybridizable", is suitable. Stable duplex formation depends on the sequence and length of the hybridizing PNA oligomer and the degree of complementarity with the target polynucleotide. Generally, the larger the hybridizing oligomer, the more mismatches may be tolerated. One skilled in the art may readily determine the degree of mismatching which may be tolerated between any given PNA oligomer and the target sequence, based upon the melting temperature, and therefore the thermal stability, of the resulting duplex.

Preferably, the thermal stability of hybrids formed by PNA oligomers is determined by way of melting, or strand dissociation, curves. The temperature of fifty percent strand dissociation is taken as the melting temperature, $T_m$, which, in turn, provides a convenient measure of stability.

For therapeutic or prophylactic treatment, the conjugates of the invention can be formulated in a pharmaceutical composition, which may include carriers, thickeners, diluents, buffers, preservatives, surface active agents and the like. Pharmaceutical compositions may also include one or more active ingredients such as antimicrobial agents, anti-inflammatory agents, anesthetics, and the like in addition to the ligand/PNA oligomer conjugate.

One preferred formulation, for intravenous or subcutaneous administration consists of sterile normal saline. For slow release from subcutaneous or intramuscular depots, the conjugates may be combined with sterile ethanol, polyethylene glycol, e.g., PEG 400, or polyethyleneglycol triricinoleate 35.

The pharmaceutical composition may be administered in a number of ways depending on whether local or systemic treatment is desired, and on the area to be treated. Administration may be performed topically (including ophthalmically, vaginally, rectally, transdermally, intranasally), orally, by inhalation, or parenterally, for example by intravenous infusion, drip or injection, or subcutaneous, intraperitoneal or intramuscular injection. Intravenous administration is utilized for rapid systemic distribution.

Anticancer conjugates according to the present invention are preferably administered by either systemic or regional perfusion, as is appropriate. According to a method of regional perfusion, the afferent and efferent vessels supplying the extremity containing the lesion are isolated and connected to a low-flow perfusion pump in continuity with an oxygenator and a heat exchanger. The iliac vessels may be used for perfusion of the lower extremity. The axillary vessels are cannulated high in the axilla for upper extremity lesions. Ligand/PNA oligomer conjugate is added to the perfusion circuit, and the perfusion is continued for an appropriate time period, e.g., one hour. Perfusion rates of from 100 to 150 ml/minute may be employed for lower extremity lesions, while half that rate should be employed for upper extremity lesions. Systemic heparinization may be used throughout the perfusion, and reversed after the perfusion is complete. This isolation perfusion technique permits administration of higher doses of chemotherapeutic agent than would otherwise be tolerated upon infusion into the arterial or venous systemic circulation.

For systemic infusion, the ligand/PNA oligomer conjugate may be delivered via a central venous catheter, which is connected to an appropriate continuous infusion device. Indwelling catheters provide long term access to the intravenous circulation for frequent administration of drugs over extended time periods. They are generally surgically inserted into the external cephalic or internal jugular vein under general or local anesthesia. The subclavian vein is another common site of catheterization. The infuser pump may be external, or may form part of an entirely implantable central venous system such as the INFUSAPORT system available from Infusaid Corp., Norwood, Mass. and the PORT-A-CATH system available from Pharmacia Laboratories, Piscataway, N.J. These devices are implanted into a subcutaneous pocket under local anesthesia. A catheter, connected to the pump injection port, is threaded through the subcdavian vein to the superior vena cava. The implant contains a supply of drug in a reservoir which may be replenished as needed by injection of additional drug from a hypodermic needle through a self-sealing diaphragm in the reservoir. Completely implantable infusers are preferred, as they are generally well accepted by patients because of the convenience, ease of maintenance and cosmetic advantage of such devices.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates. A dosage of from about 0.1 to about 3.0 mg/kg/day, more preferably from about 0.1 to about 1.0 mg/kg/day, is believed useful, based upon animal experiments where antisense DNA phosphorothioates were effective in animals in a subcutaneous/intraperitoneal dosage of 5–50 mg/kg/day.

Treatment regimens may include daily slow infusion, daily subcutaneous injection, daily transdermal patch wearing, daily nasal atomizer spray, weekly intramuscular injection, or monthly subcutaneous depot. The ligand/PNA conjugate may be delivered via slow release pledget placed for subcutaneous, intramuscular or intracranial release. Ideally, a slow release pledget may be used in place of a debulked tumor, for adjuvant therapy. See, for example, Brem et al., *Lancet* 345, 1008–1012 (1995).

Therapeutic end points can be determined by ablation of target gene expression (e.g., by Northern hybridization or PCR for detection of relevant mRNA, or Western blotting for detection of the relevant gene product), or by oblation of tumor load, viral load or disease symptoms.

Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated since they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic phosphorothioate oligonucleotides. As used herein, therapeutics is meant to include the eradication of a disease state, by killing an organism or by control of erratic or harmful cellular growth or expression.

The ligand/PNA conjugates of the invention also have diagnostic utility. With an intercalating fluorophore, such as ethidium, attached to one end of a PNA and a receptor ligand attached to the other, one may probe diagnostically for excess copies of a pathogenic gene in cells from a biopsy. Cellular binding and uptake of the conjugate via the target ligand will screen among cells for those which overexpress the receptor which correlates with pathogenesis. Following uptake of fluorophore-PNA-ligand by suspect cells, PNA hybridization with a target sequence in a pathogenic gene will allow intercalation of the fluorophore into adjacent DNA, elevating the quantum yield of its fluorescence, allowing scoring of those cells by flow cyrtometry. For example, breast cancer cells with excess copies of c-erbB2 or c-myc may be identified by ethidium-PNAs conjugated to ligands for erbB2 p185 receptor, IGF1 receptor or even α-fetoprotein. To detect pathogenic cells which do not display excess pathogenic DNA copy number, but only excess pathogenic mRNA copy number, one may substitute a fluorophore specific to RNA, such as acridine.

The practice of the invention is illustrated by the following nonlimiting examples.

EXAMPLE 1

PNA/IGF1 Peptide Conjugate: H-Gly-CCGCTTCCTTTC-Gly-Gly-Gly-Gly-D-Cys-D-Ser-D-Lys-D-Cys-NH$_2$ A. Introduction The title PNA-peptide conjugate was synthesized on solid phase with a blend of automatic and manual synthesis. The peptide segment is an analog of the IGFI protein designed by molecular modeling, to bind to the IGFI receptor. D-amino acids were utilized for synthesis to impart biological stability. The use of unnatural D-amino acids was chirally compensated by reversing the sequence of the peptide, to maintain the same sidechain conformation as in the peptide composed of naturally occurring L-amino acids. There are eight amino acids in the peptide segment, among which the four glycines at the N-terminus are designed to act as a spacer between the peptide and the PNA moieties to minimize mutual interference, as these two segments by design have independent functions. The active part is the cyclized tetrapeptide portion (D-Cys-D-Ser-D-Lys-D-Cys) of the eight amino acids.

B. Preparation of Side-chain Protected IGF1 Peptide

A peptide of the sequence Gly-Gly-Gly-Gly-Cys-Ser-Lys-Cys (SEQ ID NO:1), comprising D-Cys, D-Ser and D-Lys amino acids having protected side chains, was synthesized by FMOC coupling of FMOC-D-Cys(MOB)-OH, FMOC-D-Lys(Z)-OH, FMOC-D-Ser(Bzl)-OH and FMOC-Gly-OH in a 0.25 mmole scale as follows. Each deprotection step resulted in the removal of FMOC from the amino group of each sequentially added amino acid, while leaving side chain protecting groups (MOB, Z, Bzl) intact.

p-Methyl benzhydrylamine·HCl (1% DVP cross-linked) resin was washed twice with 10 ml NMP for 40 seconds. FMOC was removed from the resin by treatment with 20 ml of 20% piperidine/NMP for 7 minutes, followed by 50% piperidine/NMP for 10 minutes. One mmol of FMOC-D-Cys(MOB)-OH was added to the resin and activated by addition of 1 ml of 2 M DIEA/NMP, 2 ml of 0.45 M HBTU in DMF, and 1 ml of NMP. Nitrogen gas was bubbled through the mixture for 3 minutes. The nitrogen bubbling was repeated four times. The coupling reaction was allowed to proceed for 50 minutes, followed by removal of the FMOC group from the added amino acid with piperidine/NMP as above. The deblocked resin-amino acid was washed with 10 ml NMP, 10 ml for five minutes, followed by washing with 7 ml $CH_2Cl_2$ for three minutes. The resin was dried for 26 minutes. The cycle, beginning with the introduction and activation of the added amino acid, was repeated with the remaining FMOC amino acids to provide H-Gly-Gly-Gly-Gly-D-Cys(MOB)-D-Ser(Bzl)-D-Lys(Z)-D-Cys(MOB)-resin.

C. Preparation of PNA-Peptide

A 12-mer PNA chain of the sequence H-Gly CCGCTTC-CTTTC (H-Gly-SEQ ID NO:5) was synthesized as a continuation of the H-Gly-Gly-Gly-Gly-D-Cys(MOB)-D-Ser(Bzl)-D-Lys(Z)-D-Cys(MOB)-resin. The PNA sequence is complementary to the nucleotide sequence comprising codons 706–709 of the IGF1R mRNA. The complete IGF1R cDNA sequence is disclosed in Ullrich et al., *EMBO J.*, 5, 2503–2512 (1986), incorporated herein by reference. The PNA chain consists of repeating amide bond-linked N-(2-aminoethyl)-glycine units. Each N-(2-aminoethyl)-glycine unit has an attached organic base which is connected thereto by methylene carbonyl linkages. The four PNA monomers of Formulae IIIa–IIId, were purchased from Millipore Corp., Bedford, Mass., and used in the preparation.

BOC-protected PNA monomer (0.15 mmol) was coupled to the H-Gly-Gly-Gly-Gly-D-Cys(MOB)-D-Ser(Bzl)-D-Lys(Z)-D-Cys(MOB)-resin by adding a preactivated (for 2 minutes) monomer solution containing 0.10 M BOC-protected monomer, 0.08 M HBTU, and 0.20 M DIEA (base) in pyridine/DMF (1:1, v/v) (reaction volume=1.5 ml) to the peptide-resin. Coupling proceeded for 20 minutes. Qualitative ninhydrin analysis was conducted on an aliquot of the growing BOC-PNA-peptide-resin to determine if any free amine groups remained. The BOC-PNA-peptide-resin was washed twice with neat pyridine (3 ml) for two minutes, and then contacted with 3 ml of a solution of acetic anhydride/pyridine/$CH_2Cl_2$ (10:12:78, v/v/v) for five minutes, to cap any free amino groups. Any acetyl groups formed during this step where then removed by treatment with 3 ml piperidine/$CH_2Cl_2$ for five minutes. The BOC-PNA-peptide-resin was washed with 3 ml DMF/$CH_2Cl_2$ (1:1, v/v) three times, for two minutes each interval, followed by washing with 3 ml $CH_2Cl_2$ alone three times, for two minute intervals.

BOC-de protection was carried out by contacting the BOC-PNA-peptide-resin with TFA/m-cresol (95:5, v/v) for 2 minutes to remove any remaining any protecting group from the amino terminus. The treatment was then repeated. The PNA-peptide-resin was washed three times for two minute intervals with DMF/$CH_2Cl_2$ (1:1, v/V), followed by washing twice with neat pyridine for two minute intervals. The coupling/deprotection cycle with BOC-PNA monomers was repeated until the title PNA sequence was in place. Nihydrin analysis was repeated and proved negative for free amino groups. Cleavage of the completed PNA/peptide from the resins was accomplished by treatment with anhydrous HF/anisole at 0° C. for 45 minutes. The crude product was maintained in a reduced state with HSEtOH.

D. Purification of the Conjugate

The crude conjugate product was cyclized by dissolving it in 0.01 M $NaHCO_3$, pH 8.5, at 5.0 g/L, and stirred for 24 hours. The solution was frozen with dry ice-ethanol and dried under vacuum. The dried compound was assayed for free sulfhydryl groups by Ellman's reagent (DTNB assay). A negative result proved the absence of free sulfhydryl groups implying complete cyclization. The cyclized crude product was purified by reverse phase high performance liquid chromatography by a C,8 Econosil column (I.D. 10 mm, length 250 mm), (Alltech, Deerfield, Ill.) on a Waters 600 multisolvent delivery system coupled with a temperature controller maintaining the column at 50° C., and a Waters 486E variable wavelength detector, monitoring eluent absorbance at 260 nm. A single peak was observed in the HPLC chromatogram. The yield of product was almost 90%, as calculated from the area under the peak of the chromatogram.

E. Characterization of the Conjugate (a) MALDI/TOF-MS

The conjugate was characterized by MALDI-TOF mass spectroscopy (Hewlett-Packard 1700 LDI) (Pieles et al., *Nucl. Acids Res.* 21: 3191–3196, 1993). Equal volumes of a stock solution of the conjugate (in 20% methanol) at 0.5 mM and a solution of sinapinic acid (3,5-dimethoxy-4-hydroxycinnamic acid, Aldrich, Milwaukee, Wis.), was mixed well and 1 ml of the solution was placed on the tip of the probe, and the sample allowed to crystallize under vacuum. The crystallized sample was analyzed to obtain the mass of the molecule. The experimental mass of 3854.5 agreed with the calculated mass of 3850.7. The mass spectral data demonstrated that the conjugate with correct molecular mass was synthesized.

(b) SDS-Polyacrylamide Gel Electrophoresis

The PNA-peptide conjugate was also characterized by SDS-polyacrylamide gel electrophoresis. The samples were electrophoresed on "READY GELS" from Bio-Rad, Hercules, Calif., which are 4–20% acrylamide gradient Tris-Glycine gels, on a Bio-Rad Mini-Protean II Cell apparatus. The electrophoresis was conducted at 100 V, in Laemmli buffer. The gels were stained with Coomassie brilliant blue to visualize the bands. The conjugate migrated according to its molecular mass, compared to the standard molecular mass markers. This is the first demonstration that PNA-peptide conjugates could be analyzed for their identity by gel electrophoresis. In previous experiments PNAs were analyzed on native polyacrylamide gels as hybridized complexes of charged nucleic acids (Egholm et al., *Nature* 365: 566–568, 1993).

F. Serum Stability of the PNA-peptide Conjugate

The title conjugate was incubated in 10% fetal bovine serum/PBS for 12 hours and 24 hours. After the incubation, one volume of acetonitrile was added to precipitated protein, which was pelleted by centrifugation. Free conjugate in the supernatant was dried under vacuo. It was then analyzed by reverse phase HPLC as described above. The stability of the conjugate was confirmed.

G. Control PNA

A PNA control sequence, Gly-CCGCTTCCTTTC-CONH$_2$ (Gly-SEQ ID NO:5-CONH$_2$) was custom synthesized by PerSeptive Biosystems, Framingham, Mass.

H. Synthesis of PNA-peptide-fluorescein and PNA-fluorescein conjugates

The purified title PNA-peptide conjugate (H-Gly-SEQ ID NO:5/SEQ ID NO:1) and control PNA (H-Gly-SEQ ID NO:5-CONH$_2$) were fluoresceinated by treating them with a 20-fold excess of FITC in 0.2 M phosphate buffer, pH 8.5, for two hours with constant stirring. The products were purified first by passing through a NAP-10 G-25 Sephadex column (Pharmacia Biotech Inc., Piscataway, N.J.) and then on a G-50 Sephadex column. The procedure results in the attachment of a fluorescein group to the N-terminus of the PNA oligomer.

I. Cellular Uptake Studies With PNA-peptide-fluorescein and PNA-fluorescein conjugates P6 cells, which are murine Balb/c3T3 cells transfected with human insulin-like growth factor receptor (IGF1R) gene, overexpress IGF1R. The cells were plated on LAB TEK 8 well tissue culture "CHAMBER SLIDES" from Nunc, Inc., Naperville, Ill. in 10% FBS/DMEM at a concentration of 20,000 cells/chamber. The cells were allowed to attach and grow for 24 hours in a humidified cell incubator with 5% $CO_2$ at 37° C. The attached cells were then washed with serum-free DMEM and PBS. The cells were incubated for 4 hours at 37° C. with 1 μM of the fluoresceinated PNA-peptide (H-Gly-SEQ ID NO:5/SEQ ID NO: 1) or fluoresceinyl-PNA (H-Gly-SEQ ID NO:5-CONH$_2$) in serum-free DMEM. Human Jurkat cells, which have very low copies of IGF1R (Lal et al., *Leukemia Res.* 17, 31–35, 1983) were used as a negative control. The Jurkat cells were grown in 10% FBS/RPMI. The Jurkat cells were treated in the same manner as the P6 cells, except that necessary modifications were made in handling the cells as they grow in suspension.

At the conclusion of the incubation period the cells were washed thrice with PBS and then fixed with 1% paraformaldehyde/PBS for one hour. Cells were next washed once with buffer (from "ANTI-FADE" kit, Molecular Probes, Eugene, Oreg.). The chambers were removed and excess liquid drained off. One drop of the same buffer was put on the places where the chambers were located, covered with cover-slips, then sealed.

The fixed slides were analyzed under laser confocal fluorescence and phase contrast microscopy to observe the cellular uptake of the fluorescent oligomers. Confocal microscopy allowed observation of different planar sections of the cells which eliminated the possibility of picking up signals residing on the cell surface. This is an advantage over conventional fluorescence microscopy, which cannot differentiate between signals inside and outside of the cells.

The results are shown in the figures. FIGS. 1A, 2A, 3A and 4A comprise phase contrast microphotographs of P6 cells with fluorescein (FIG. 1A), P6 cells with fluoresceinyl-PNA (FIG. 2A), P6 cells with fluoresceinyl-PNA-peptide (FIG. 3A) and Jurkat cells with fluoresceinyl-PNA-peptide (FIG. 4A). FIGS. 1B, 2B, 3B and 4B are fluorescence microphotographs of P6 cells with fluorescein (FIG. 1B), P6 cells with fluoresceinyl-PNA (FIG. 2B), P6 cells with fluoresceinyl-PNA-peptide (FIG. 3B) and Jurkat cells with fluoresceinyl-PNA-peptide (FIG. 4B). FIG. 3C is a view superimposing the fluorescence field of FIG. 31B over the phase contrast view of FIG. 3A.

As may be appreciated from the figures, conjugation of the PNA oligomer to IGF1 peptide results in the receptor-specific internalization of the conjugate into the cell. Fluorescence is visible with in the cells in FIG. 3B (fluorescinated PNA-peptide), but not in FIGS. 1B (fluorescein) and 2B (fluoresceinyi-PNA). The absence of uptake of fluorescein or the fluoresceinyl-PNA molecule also indicated that the uptake of the conjugate was not mediated by the fluorescein moiety. Furthermore, when exposed to the fluorescinated PNA-peptide conjugate, the Jurkat cells exhibited almost no fluorescein signal (FIG. 4B), indicating that the uptake of the conjugate was mediated by the peptide moiety. Jurkat cells do not express the IGF1R receptor.

Figures 3A, 3B:
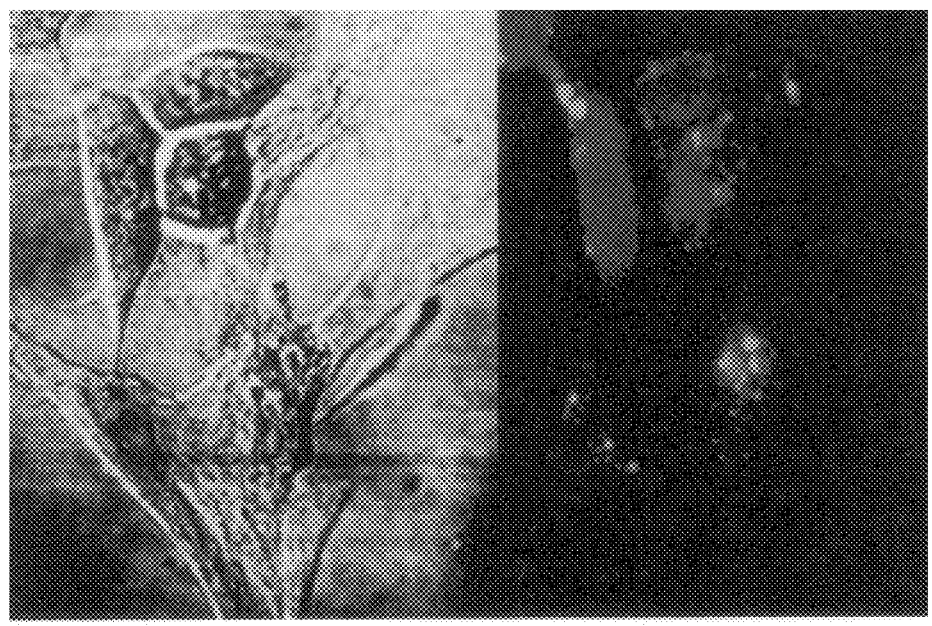
FIGS. 3A and 3B are similar to FIGS. 2A and 2B except that P6 cells were exposed to a fluoresceinyl-PNA-peptide comprising the same fluoresceinated PNA oligomer, conjugated to the peptide (Gly)$_4$-D-Cys-D-Ser-D-Lys-D-Cys (H-Gly-SEQ ID NO:5/SEQ ID NO: 1).
Figure 3C:
FIG. 3C represents the same phase contrast view of FIG. 3A, but with the fluorescence field of FIG. 3B superimposed thereon to identify the fluorescein signal within the cellular boundary.
Figures 4A, 4B:
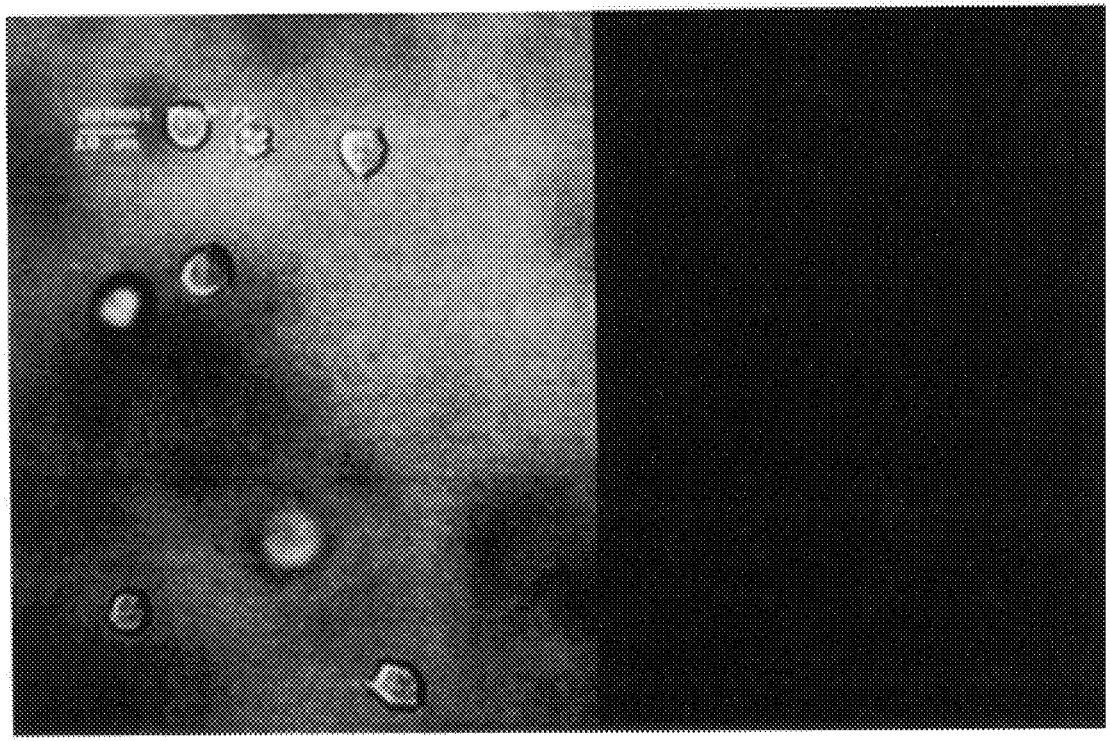
FIGS. 4A and 4B are similar to FIGS. 3A and 3B except that Jurkat cells were used instead of P6 cells.

FIG. 3C, which is a superimposition of the FIG. 3B fluorescence microphotograph on the FIG. 3A phase contrast view, shows that the dye was in fact taken up by the P6 cells. Since the observed field was a planar section from inside of the cells, the conjugate is observed to have been internalized.

J. Synthesis of [$^{14}$C]PNA-peptide and [$^{14}$C]PNA conjugaates

A control PNA-peptide with the peptide sequence Gly-Gly-Gly-Gly-D-Cys-D-Ala-D-Ala-D-Cys (SEQ ID NO:6) and the same PNA segment as the title compound (H-Gly-SEQ ID NO:5) was synthesized. The control PNA-peptide (H-Gly-SEQ ID NO:5/SEQ ID NO:6), the control PNA (H-Gly-SEQ ID NO:5-CONH$_2$) and the title PNA-peptide conjugate (H-Gly-SEQ ID NO:5/SEQ ID NO: 1) were radioactively labeled by reductive methylation with [$^{14}$C] formaldehyde as described by Hughes et al., *Pharm Res.* 12: 817–824 (1995). Briefly, PNA and PNA-peptides (100 nmol) were dissolved in 0.1 ml of 0.2 M sodium phosphate buffer (pH 7.5, to minimize lysine methylation) and 500 nmoles [$^{14}$C]formaldehyde (#NEC-039H, 40–60 Ci/mol, Dupont-NEN, Boston, Mass.) and incubated for 2 hours at room temperature with periodic vortexing. Sodium cyanoborohydride (0.1 ml μl of a fresh 100 mM solution) was then added to the mixture to reduce the Schiffs base, and the incubation was continued for an additional 4 hours with periodic vortexing. The [$^{14}$C]PNA derivatives were purified by gel filtration on NAP10 columns (#17-0854-01, Pharmacia, Milwaukee, Wis.). Homogeneity was evaluated by TLC of a small aliquot on cellulose plates (#1366061, Eastman Kodak, Rochester, N.Y.) developed with n-butanol/glacial acetic acid/H$_2$O (4:1:5). Specific activities of the labeled oligonucleotides were estimated by measuring concentrations from $A_{260}$ in UV-absorbing TLC bands extracted with water, and $^{14}$C radioactivity using liquid scintillation counting at 75% counting efficiency. The specific activities of several preparations ranged from 5.3–11 Ci/mol.

K. Thermal Denaturation Studies

Figure 5:
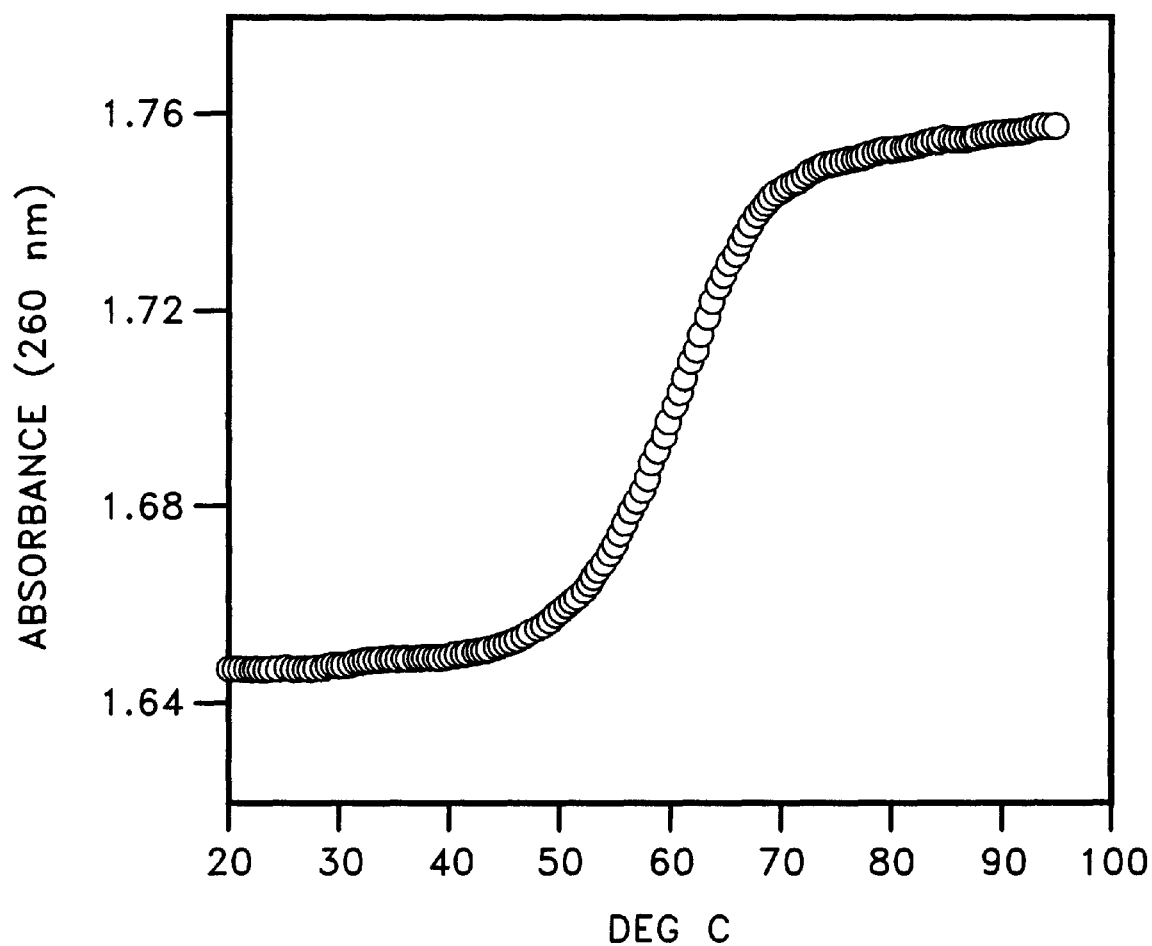
FIG. 5 contains the melting temperature curve for the duplex consisting of the PNA-peptide conjugate H-Gly-CCGCTTCCTTTC-(Gly)$_4$-DCys-D-Ser-D-Lys-D-Cys-NH$_2$ (H-Gly-SEQ ID NO:5/SEQ ID NO:1) and its complementary 12-mer GAAAGGAAGC GG (SEQ ID NO:7) (open circles).

Thermal denaturation experiments of an equimolar mixture of the purified title PNA-peptide (H-Gly-SEQ ID NO:5/SEQ ID NO: 1) or control PNA (H-Gly-SEQ ID NO:5-CONH$_2$) and its complementary 12-mer DNA target GAAAGGAAGCGG (SEQ ID NO:7) in 10 mM Tris-HCl, pH 8.0 and 100 mM NaCl, was performed on a Cary 3E UV-vis spectrophotometer equipped with a multicell holder and a temperature controller (Varian, Palo Alto, Calif.). The rate of increase of the temperature was 1° C/min, from 10° C. to 90° C. All $T_m$ values were calculated from the first derivative of the melting curve and the final value is the average of triplicate experiments. The two melting curves were identical, yielding a Tm of 60°±1° C. (FIG. 5). This study demonstrates that the peptide moiety does not interfere with the hybridization of the PNA to its complementary DNA target. Such an effect on hybridization would be apparent as a difference in Tm as between the melting of the hybrid formed by the PNA-peptide conjugate and its complementary DNA target on the one hand, and the melting of the hybrid formed by the PNA segment and the same complementary DNA target on the other hand.

L. Cellular Uptake Studies With [$^{14}$C]PNA-peptide and [$^{14}$C]PNA Conjugates Uptake studies with radiolabeled PNA derivatives were carried out. P6 or Jurkat cells above were plated in 12.5 cm$^2$ flasks and grown for two days to 50–80% confluence, on the order of 10$^6$ cells per flask. The medium was then removed and replaced with fresh medium containing 1 μM of the various [$^{14}$C]PNA derivatives, pre-warmed to 37° C.; background cells received medium with no [$^{14}$C]PNA derivatives. After incubation for various times, attached cells were washed directly in the flasks using four washes—once with fresh medium, once with PBS, once with high salt/low pH buffer, and once with PBS. This procedure had the advantage of removing both non-internalized oligonucleotide and any dead cells, which can accumulate large amounts of oligonucleotide and thereby skew any uptake measurements.

After the final wash, the cells were lysed in 1 ml of 1% SDS in H$_2$O, and the samples were processed for total protein measurement and liquid scintillation counting. 50 μl of the lysate was allocated for total protein measurement, and $^{14}$C activity in the remaining lysate was measured by liquid scintillation counting, from which background counts were subtracted. Background samples from control lysates not treated with [$^{14}$C]PNA derivatives typically yielded 12–15 cpm, corresponding to less than 1 pmol experimental sample with twice the background cpm would contain 0.2–1 pmol, depending on the specific activity, which may be considered the limit of detection.

Control samples of varying confluence were trypsinized following the last wash, resuspended in PBS for cell counting, and then lysed to obtain total protein values. This allowed the generation of a standard curve corresponding to total protein vs. cell number. The curve was used to estimate cell counts from the total protein measurements of treated cells, and radioactivity counts were used to calculate pmoles of oligonucleotide using the specific activity of each labeled oligonucleotide. Values for cell number and pmoles of cell-associated oligonucleotide were therefore obtained for each treated sample. Estimates of cell volume were obtained by microscopic evaluation of cell diameters using a micrometer and subsequent calculation of an average cell volume.

Figure 6:
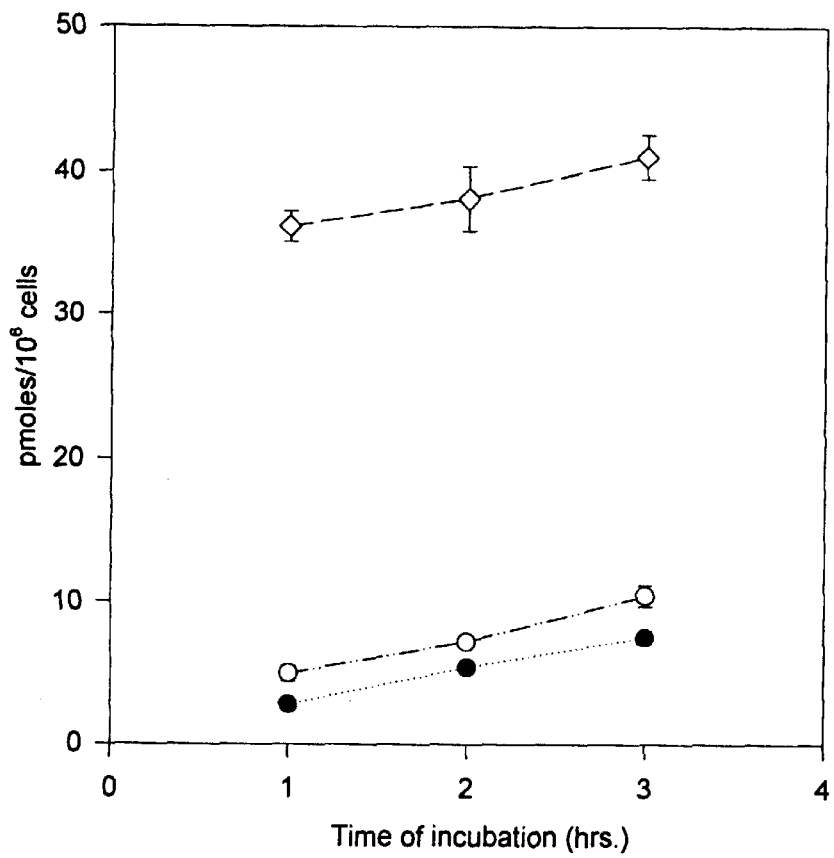
FIG. 6 is a plot of the P6 cell uptake of the [$^{14}$C]-PNA H-Gly-SEQ ID NO:5-CONH$_2$ (●), the [$^{14}$C]-PNA-peptide H-Gly-SEQ ID NO:5/SEQ ID NO: 1 (◇) and the [$^{14}$C]-PNA-peptide H-Gly-CCGCTTCCTTTC-(Gly$_4$)-D-Cys-D-Ala-D-Ala-D-Cys-NH$_2$ (H-Gly-SEQ ID NO:5/SEQ ID NO:6) (○). The data are presented in terms of pmoles oligonucleotide per 10$^6$ cells. Each data point represents the mean ±SE of three replicates.
Figure 7:
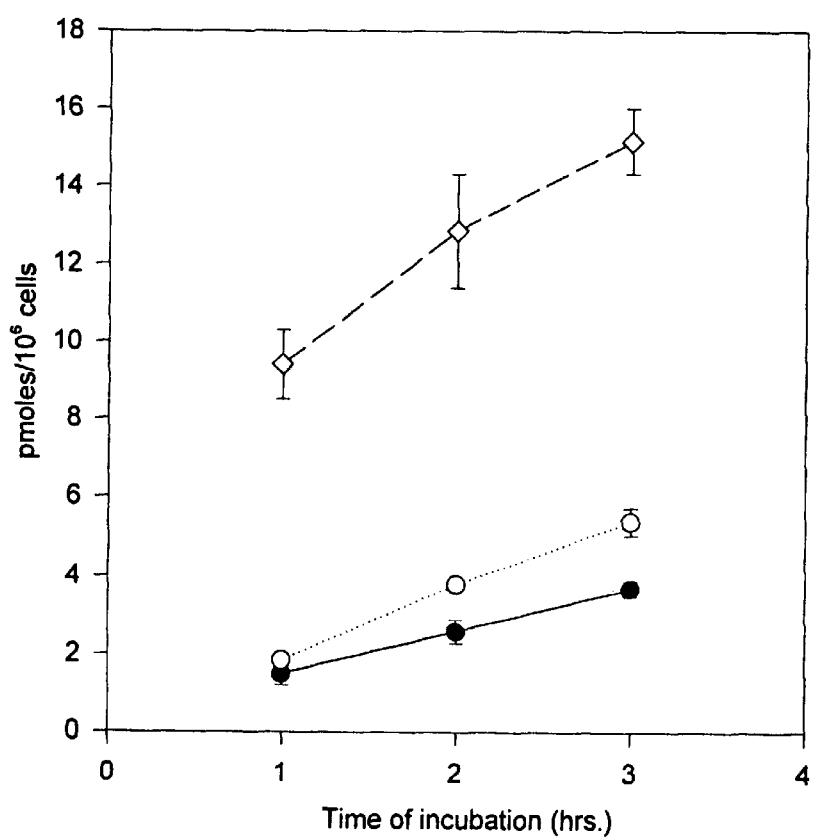
FIG. 7 is similar to FIG. 6 and represents the Balb/c3T3 cell uptake of the same PNA derivatives of FIG. 6.
Figure 8:
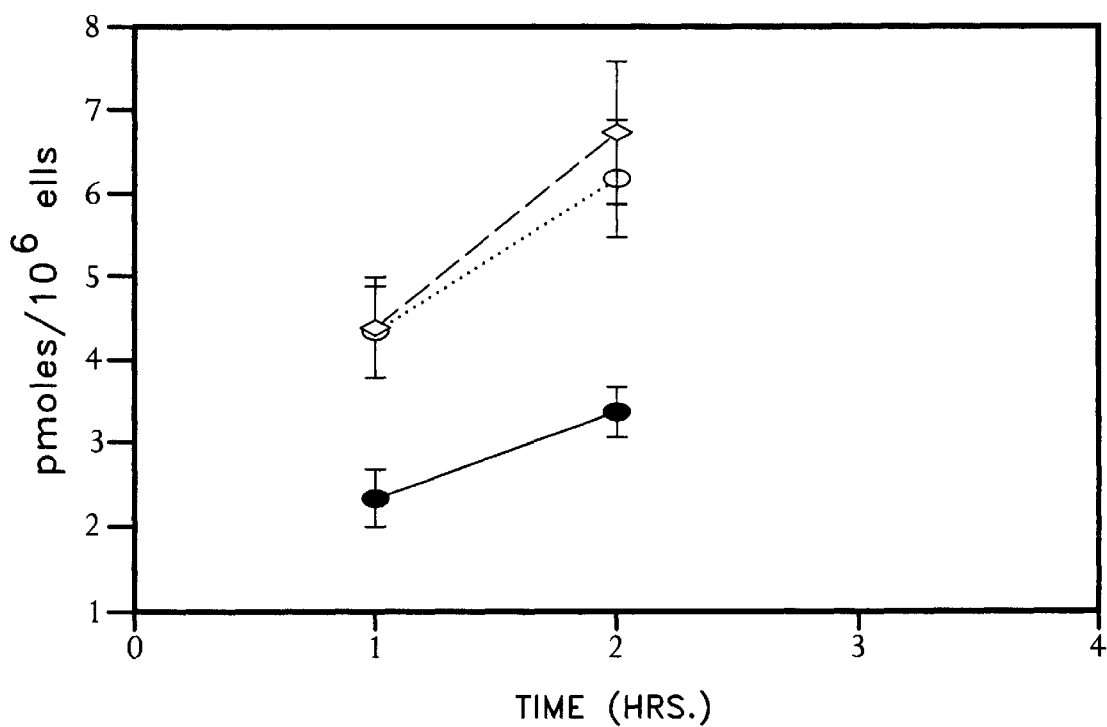
FIG. 8 is similar to FIG. 6, and represents the Jurkat cell uptake of the same PNA derivatives of FIG. 6.

The results obtained with $^{14}$C-labeled PNA and PNA-peptides were comparable to the results obtained with the fluoresceinated compounds. Uptake measurements with P6 cells showed five-fold more uptake by the title PNA-peptide conjugate than by the control PNA or the control PNA-peptide (FIG. 6). Similarly, uptake experiments with Balb/c3T3 cells, the parental line from which P6 cells were derived, which expresses low levels of IGF1R, displayed lower uptake of the title PNA-peptide conjugate, but still a four-fold excess relative to the controls (FIG. 7). In contrast, uptake experiments with Jurkat cells, which express virtually no IGF1R, displayed little preferential uptake of the title PNA-peptide conjugate relative to the controls (FIG. 8).

EXAMPLE 2

PNA/IGF1 Peptide Conjugate: H-Gly-TCCGGAGCCA GACTT-(CH$_2$)$_5$CO(O)-D-Cys-D-Arg-D-Arg-D-Ser-D-Ser-D-Ser-Gly-D-Tyr-Gly-D-Thr-Gly-D-Cys The synthetic procedure of Example 1 was followed to form the title compound which is a conjugate of the peptide Cys-Arg-Arg-Ser-Ser-Ser-Gly-Tyr-Gly-Thr-Gly-Cys (SEQ ID NO:3) formed of D-amino acids, and the PNA chain of the sequence H-Gly-TCCGGAGCCA GACTT (H-Gly-SEQ ID NO:2). The PNA sequence is complementary to the nucleotide sequence comprising codons 2–6 of the IGF1R mRNA. The following additional protected D-amino acids were utilized to form the title conjugate: N-α-Fmoc-N$^G$-4-methoxy-2,3,6-trimethylbenzenesulfonyl-D-arginine; N-α-Fmoc-O-trityl-D-tyrosine; and N-α-Fmoc-O-benzyl-D-threonine. Also, following attachment of the N-terminal cysteine residue and removal of that residue's FMOC blocking group, the protected peptide-resin was reacted with N-FMOC-ε-aminocaproic acid to add the linking group —(CH$_2$)$_5$C(O)— to the N-terminus of the growing peptide.

The present invention may be embodied in other specific forms without departing from the spirit or essential attributes thereof and, accordingly, reference should be made to the appended claims, rather than to the foregoing specification, as indicating the scope of the invention.

All references cited herein with respect to synthetic, preparative and analytical procedures are incorporated herein by reference.

What is claimed is:

1. A conjugate comprising a peptide nucleic acid oligomer conjugated to a peptide which is capable of binding with a cell surface receptor, said peptide being attached to said peptide nucleic acid oligomer directly by a chemical bond or by a linker which comprises one or more amino acids.

2. A conjugate according to claim 1 wherein the oligomer contains at least one subunit which is a peptide nucleic acid subunit of the formula:

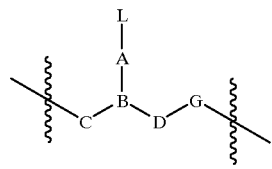
(I)

wherein:

L is one of the adenine, thymine, cytosine or guanine heterocyclic bases of the oligomer;

C is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$ alkyl, aryl, aralkyl, heteroaryl, hydroxy, $(C_1-C_6)$ alkoxy, $(C_1-C_6)$ alkylthio, $NR^3R^4$ and $SR^5$, where each of $R^3$ and $R^4$ is independently selected from the group consisting of hydrogen, $(C_1-C_4)$ alkyl, hydroxy- or alkoxy- or alkylthio-substituted $(C_1-C_4)$ alkyl, hydroxy, alkoxy, alkylthio and amino; and $R^5$ is hydrogen, $(C_1-C_6)$ alkyl, hydroxy-, alkoxy-, or alkylthio-substituted $(C_1-C_6)$ alkyl, or $R^6$ and $R^7$ taken together complete an alicyclic or heterocyclic system;

D is $(CR^6R^7)_z$ where $R^6$ and $R^7$ are as defined above;

each of y and z is zero or an integer from 1 to 10, the sum y+z being greater than 2 but not more than 10;

G is —$NR^3CO$—, —$NR^3CS$—, —$NR^3SO$— or —$NR^3SO_2$—, in either orientation, where $R^3$ is as defined above;

each pair of A and B is selected such that:

(a) A is a group of formula (IIa), (IIb) or (IIc) and B is N or $R^3N^+$; or (b) A is a group of formula (IId) and B is CH;

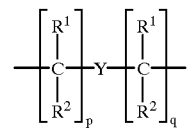
(IIa)

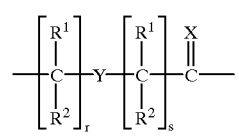
(IIb)

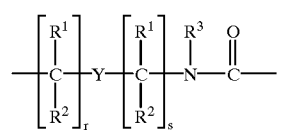
(IIc)

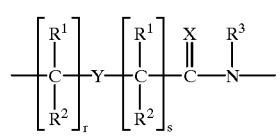
(IId)

wherein:

X is O, S, Se, $NR^3$, $CH_2$ or $C(CH_3)_2$;

Y is a single bond, O, S or $NR^4$;

each of p and q is zero or an integer from 1 to 5;

each of r and s is zero or an integer from 1 to 5;

each $R^1$ and $R^2$ is independently selected from the group consisting of hydrogen, $(C_1-C_4)$ alkyl which may be hydroxy- or alkoxy- or alkylthio-substituted, hydroxy, alkoxy, alkylthio, amino and halogen.

3. A conjugate according to claim 2 wherein A is —$CH_2CO$—, B is N, C is $CH_2CH_2$ and D is $CH_2$.

4. A conjugate according to claim 2 wherein all of the subunits of the peptide nucleic acid oligomer are peptide nucleic acid subunits.

5. A conjugate according to claim 3 wherein all of the subunits of the peptide nucleic acid oligomer are peptide nucleic acid subunits.

6. A conjugate according to claim 4 wherein the peptide nucleic acid oligomer has a subunit sequence such that the oligomer is capable of forming (i) a triplex with a dsDNA segment or (ii) a duplex with a ssDNA segment or an mRNA segment, to inhibit expression of a gene.

7. A conjugate according to claim 6 wherein the oligomer is capable of forming a duplex with a portion of an mRNA transcript lying within about 100 nucleotides upstream or downstream of the translation initiation codon, or within about 100 nucleotides of the 5'-untranslated region.

8. A conjugate comprising a peptide nucleic acid oligomer conjugated to a ligand which is capable of binding with a cell surface receptor, which peptide nucleic acid oligomer has a subunit sequence capable of inhibiting expression of a gene which encodes the cell surface receptor.

9. A conjugate according to claim 8 wherein the oligomer contains at least one subunit which is a peptide nucleic acid subunit of the formula:

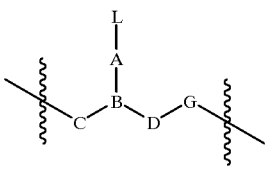 (I)

wherein:

L is one of the adenine, thymine, cytosine or guanine heterocyclic bases of the oligomer;

C is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$ alkyl, aryl, aralkyl, heteroaryl, hydroxy, $(C_1-C_6)$ alkoxy, $(C_1-C_6)$ alkylthio, $NR^3R^4$ and $SR^5$, where each of $R^3$ and $R^4$ is independently selected from the group consisting of hydrogen, $(C_1-C_4)$ alkyl, hydroxy- or alkoxy- or alkylthio-substituted $(C_1-C_4)$ alkyl, hydroxy, alkoxy, alkylthio and amino; and $R^5$ is hydrogen, $(C_1-C_6)$ alkyl, hydroxy-, alkoxy-, or alkylthio-substituted $(C_1-C_6)$ alkyl, or $R^6$ and $R^7$ taken together complete an alicyclic or heterocyclic system;

D is $(CR^6R^7)_z$ where $R^6$ and $R^7$ are as defined above;

each of y and z is zero or an integer from 1 to 10, the sum y+z being greater than 2 but not more than 10;

G is $-NR^3CO-$, $-NR^3CS-$, $-NR^3SO-$ or $-NR^3SO_2-$, in either orientation, where $R^3$ is as defined above;

each pair of A and B is selected such that:
(a) A is a group of formula (IIa), (IIb) or (IIc) and B is N or $R^3N^+$; or
(b) A is a group of formula (IId) and B is CH;

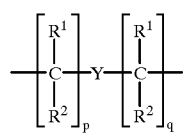 (IIa)

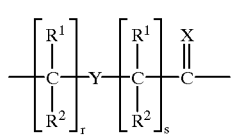 (IIb)

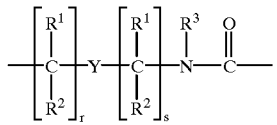 (IIc)

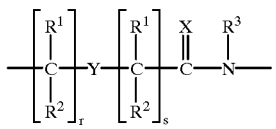 (IId)

wherein:

X is O, S, Se, $NR^3$, $CH_2$ or $C(CH_3)_2$;

Y is a single bond, O, S or $NR^4$;

each of p and q is zero or an integer from 1 to 5;

each of r and s is zero or an integer from 1 to 5;

each $R^1$ and $R^2$ is independently selected from the group consisting of hydrogen, $(C_1-C_4)$ alkyl which may be hydroxy- or alkoxy- or alkylthio-substituted, hydroxy, alkoxy, alkylthio, amino and halogen.

10. A conjugate according to claim 9 wherein the ligand is selected from the group consisting of proteins, glycoproteins, peptides, steroids, carbohydrates, lipids and vitamins.

11. A conjugate according to claim 10 wherein the ligand is a peptide.

12. A conjugate comprising a peptide nucleic acid oligomer conjugated to a peptide which is capable of binding with a cell surface receptor which peptide is selected from the group consisting of insulin growth factor-1 peptides, epidermal growth factor peptides, *Escherichia coli* heat-stable enterotoxin peptides, transforming growth factor-a peptides and heregulin peptides.

13. A conjugate according to claim 12 wherein the peptide is an insulin growth factor-1 peptide.

14. A conjugate according to claim 13 wherein the insulin growth factor-1 peptide comprises an amino acid sequence selected from the group consisting of SEQ ID NO:1 and SEQ ID NO:3.

15. A conjugate according to claim 14 wherein the insulin growth factor-1 peptide comprises at least one D-amino acid.

16. A conjugate according to claim 15 wherein the cysteine residues of the insulin growth factor-1 peptide form a cysteine-cysteine disulfide bond.

17. A conjugate according to claim 13 wherein the peptide nucleic acid oligomer has a sequence capable of inhibiting expression of the gene which encodes the insulin growth factor-1 receptor.

18. A conjugate according to claim 17 wherein the peptide nucleic acid oligomer comprises a peptide nucleic acid subunit sequence selected from the group consisting of SEQ ID NO:2 and SEQ ID NO:5.

19. A method for inhibiting expression of a gene in an organism comprising administering to the organism a conjugate according to claim 6.

20. A method for killing a pathogenic organism comprising contacting said organism with a conjugate comprising a peptide nucleic acid oligomer conjugated to a peptide, which peptide is capable of binding to a cell surface receptor and (a) contains at least one D-amino acid, and/or (b) is attached to the peptide nucleic acid oligomer directly by a chemical bond or by a linker which comprises one or more amino acids, wherein the peptide nucleic acid oligomer binds specifically to a target polynucleotide sequence of said pathogenic organism.

21. A method according to claim 20 wherein the pathogenic organism is selected from the group consisting of viruses, bacteria, and eukaryotic parasites.

22. A method for improving the cellular uptake of a peptide nucleic acid oligomer comprising conjugating the oligomer to a peptide which is capable of binding to a cell surface receptor wherein the peptide facilitates the cellular uptake of the conjugate and is characterized by at least one of the following features: (a) the peptide is selected from the group consisting of insulin growth factor-1 peptides, epidermal growth factor peptides, *Escherichia coli* heat-stable enterotoxin peptides, transforming growth factor-a peptides and heregulin peptides, (b) the peptide contains at least one D-amino acid, or (c) the peptide is attached to the peptide nucleic acid oligomer directly by a chemical bond or by a linker which comprises one or more amino acids, wherein the peptide nucleic acid oligomer.

23. A conjugate according to claim 10 wherein the ligand is covalently linked to the peptide nucleic acid oligomer.

24. A conjugate comprising a peptide nucleic acid oligomer conjugated to a peptide which is capable of binding with a cell surface receptor, which peptide comprises at least one D-amino acid.

25. A conjugate according to claim 24 wherein the peptide facilitates receptor-mediated uptake of the peptide nucleic acid oligomer into a cell.

26. A conjugate according to claim 24 wherein the oligomer contains at least one subunit which is a peptide nucleic acid subunit of the formula:

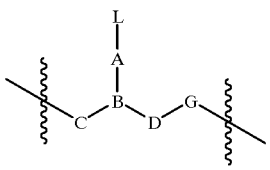

(I)

wherein:

L is one of the adenine, thymine, cytosine or guanine heterocyclic bases of the oligomer;

C is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$ alkyl, aryl, aralkyl, heteroaryl, hydroxy, $(C_1-C_6)$ alkoxy, $(C_1-C_6)$ alkylthio, $NR^3R^4$ and $SR^5$, where each of $R^3$ and $R^4$ is independently selected from the group consisting of hydrogen, $(C_1-C_4)$ alkyl, hydroxy- or alkoxy- or alkylthio-substituted $(C_1-C_4)$ alkyl, hydroxy, alkoxy, alkylthio and amino; and $R^5$ is hydrogen, $(C_1-C_6)$ alkyl, hydroxy-, alkoxy-, or alkylthio-substituted $(C_1-C_6)$ alkyl, or $R^6$ and $R^7$ taken together complete an alicyclic or heterocyclic system;

D is $(CR^6R^7)_z$ where $R^6$ and $R^7$ are as defined above;

each of y and z is zero or an integer from 1 to 10, the sum y+z being greater than 2 but not more than 10;

G is $-NR^3CO-$, $-NR^3CS-$, $-NR^3SO-$ or $-NR^3SO_2-$, in either orientation, where $R^3$ is as defined above;

each pair of A and B is selected such that:

(a) A is a group of formula (IIa), (IIb) or (IIc) and B is N or $R^3N^+$; or (b) A is a group of formula (IId) and B is CH;

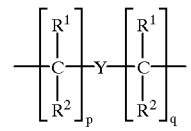

(IIa)

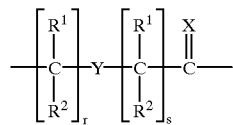

(IIb)

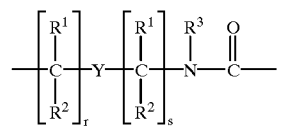

(IIc)

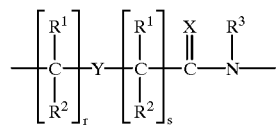

(IId)

wherein:

X is O, S, Se, $NR^3$, $CH_2$ or $C(CH_3)_2$;

Y is a single bond, O, S or $NR^4$;

each of p and q is zero or an integer from 1 to 5;

each of r and s is zero or an integer from 1 to 5;

each $R^1$ and $R^2$ is independently selected from the group consisting of hydrogen, $(C_1-C_4)$ alkyl which may be hydroxy- or alkoxy- or alkylthiosubstituted, hydroxy, alkoxy, alkylthio, amino and halogen.

27. A conjugate according to claim 25 wherein all of the subunits of the peptide nucleic acid oligomer are peptide nucleic acid subunits.

28. A conjugate according to claim 12 wherein the oligomer contains at least one subunit which is a peptide nucleic acid subunit of the formula:

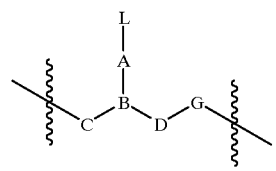

(I)

wherein:

L is one of the adenine, thymine, cytosine or guanine heterocyclic bases of the oligomer;

C is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$ alkyl, aryl, aralkyl, heteroaryl, hydroxy, $(C_1-C_6)$ alkoxy, $(C_1-C_6)$ alkylthio, $NR^3R^4$ and $SR^5$, where each of $R^3$ and $R^4$ is independently selected from the group consisting of hydrogen, $(C_1-C_4)$ alkyl, hydroxy- or alkoxy- or alkylthiosubstituted ($C_1$–$C_4$) alkyl, hydroxy, alkoxy, alkylthio and amino; and $R^5$ is hydrogen, ($C_1$–$C_6$) alkyl, hydroxy-, alkoxy-, or alkylthio-substituted ($C_1$–$C_6$) alkyl, or $R^6$ and $R^7$ taken together complete an alicyclic or heterocyclic system;

D is $(CR^6R^7)_z$ where $R^6$ and $R^7$ are as defined above;

each of y and z is zero or an integer from 1 to 10, the sum y+z being greater than 2 but not more than 10;

G is —$NR^3CO$—, —$NR^3CS$—, —$NR^3SO$— or —$NR^3SO_2$—, in either orientation, where $R^3$ is as defined above;

each pair of A and B is selected such that:
(a) A is a group of formula (IIa), (IIb) or (IIc) and B is N or $R^3N^+$; or
(b) A is a group of formula (IId) and B is CH;

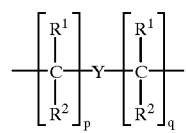
(IIa)

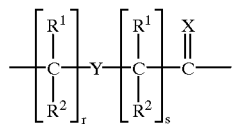
(IIb)

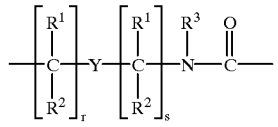
(IIc)

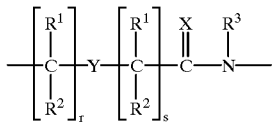
(IId)

wherein:
X is O, S, Se, $NR^3$, $CH_2$ or $C(CH_3)_2$;
Y is a single bond, O, S or $NR^4$;
each of p and q is zero or an integer from 1 to 5;
each of r and s is zero or an integer from 1 to 5;
each $R^1$ and $R^2$ is independently selected from the group consisting of hydrogen, ($C_1$–$C_4$) alkyl which may be hydroxy- or alkoxy- or alkylthio-substituted, hydroxy, alkoxy, alkylthio, amino and halogen.

29. A conjugate according to claim 28 wherein A is —$CH_2CO$—, B is N, C is $CH_2CH_2$ and D is $CH_2$.

30. A conjugate according to claim 28 wherein all of the subunits of the peptide nucleic acid oligomer are peptide nucleic acid subunits.

31. A conjugate according to claim 9 wherein A is —$CH_2CO$—, B is N, C is $CH_2CH_2$ and D is $CH_2$.

32. A conjugate according to claim 9 wherein all of the subunits of the peptide nucleic acid oligomer are peptide nucleic acid subunits.

33. A conjugate according to claim 1 wherein the linker comprises one or more glycine residues.

34. A conjugate according to claim 1 prepared by synthesizing the peptide, and then synthesizing the peptide nucleic acid oligomer as an extension of the peptide nucleic acid oligomer.

* * * * *